US009222832B2

(12) United States Patent
Kulcke

(10) Patent No.: US 9,222,832 B2
(45) Date of Patent: Dec. 29, 2015

(54) DEVICE AND METHOD FOR DETECTING AND MONITORING INGREDIENTS OR PROPERTIES OF A MEASUREMENT MEDIUM, IN PARTICULAR OF PHYSIOLOGICAL BLOOD VALUES

(75) Inventor: Axel Kulcke, Weichselbaum (AT)

(73) Assignee: Senspec GmbH, Rostock (DE)

( * ) Notice: Subject to any disclaimer, the term of this patent is extended or adjusted under 35 U.S.C. 154(b) by 234 days.

(21) Appl. No.: 13/699,488

(22) PCT Filed: Jun. 21, 2011

(86) PCT No.: PCT/EP2011/060337
§ 371 (c)(1),
(2), (4) Date: Nov. 21, 2012

(87) PCT Pub. No.: WO2011/161102
PCT Pub. Date: Dec. 29, 2011

(65) Prior Publication Data
US 2013/0066172 A1 Mar. 14, 2013

(30) Foreign Application Priority Data

Jun. 22, 2010 (EP) .................................... 10166854
Apr. 21, 2011 (EP) .................................... 11163361

(51) Int. Cl.
*A61B 5/1455* (2006.01)
*G01J 3/18* (2006.01)
(Continued)

(52) U.S. Cl.
CPC .............. *G01J 3/1838* (2013.01); *A61B 5/1455* (2013.01); *A61B 5/14532* (2013.01); *A61B 5/6801* (2013.01); *A61B 5/7239* (2013.01);
(Continued)

(58) Field of Classification Search
CPC ............. A61B 5/1455; A61B 5/14551; A61B 5/14532; A61B 5/68; A61B 5/6801; G01J 3/0256; G01J 3/1838
USPC ........................................... 600/310, 322, 323
See application file for complete search history.

(56) References Cited

U.S. PATENT DOCUMENTS 5,159,199 A 10/1992 LaBaw
5,348,003 A * 9/1994 Caro ............................. 600/310
(Continued)

FOREIGN PATENT DOCUMENTS

JP H07-503863 A 4/1995
JP H07-308312 A 11/1995
(Continued)

OTHER PUBLICATIONS

English Translation of Japanese Office Action Corresponding to JP2013-515863 Mailed on Apr. 7, 2015.

*Primary Examiner* — Eric Winakur
(74) *Attorney, Agent, or Firm* — Davis & Bujold, P.L.L.C.; Michael J. Bujold

(57) ABSTRACT

The invention relates to a device for detecting and monitoring ingredients or properties of a measurement medium, for example physiological blood values, wherein said device contains a light source (20) for generating broad-spectrum measurement light (2) and for acting on a measurement area (3), and means (9) for fanning out the analysis light (4) reflected by the measurement area (3). The device also has a sensor array (11) for picking up the fanned light. The sensor array (11), the light source (20) and the means for dispersing the analysis light (4) are arranged as a compact unit in a housing.

33 Claims, 11 Drawing Sheets

(51) Int. Cl.
   *A61B 5/00* (2006.01)
   *A61B 5/145* (2006.01)
   *G01J 3/02* (2006.01)
   *G01J 3/28* (2006.01)
   *G01J 3/42* (2006.01)
   *G01N 21/31* (2006.01)

(52) U.S. Cl.
   CPC .............. *G01J 3/021* (2013.01); *G01J 3/0256* (2013.01); *G01J 3/0264* (2013.01); *G01J 3/2803* (2013.01); *G01J 3/42* (2013.01); *G01N 21/31* (2013.01); *G01N 2021/3144* (2013.01); *G01N 2201/062* (2013.01)

(56) References Cited

U.S. PATENT DOCUMENTS

| | | |
|---|---|---|
| 5,361,758 A | 11/1994 | Hall et al. |
| 6,049,727 A | 4/2000 | Crothall |
| 6,078,828 A | 6/2000 | Yasuda et al. |
| 6,315,955 B1 | 11/2001 | Klein |
| 7,383,077 B2 * | 6/2008 | Zeng ............................ 600/473 |
| 2003/0071216 A1 | 4/2003 | Rabolt et al. |
| 2005/0154277 A1 | 7/2005 | Tang et al. |
| 2005/0267346 A1 | 12/2005 | Faber et al. |
| 2007/0216898 A1 | 9/2007 | Gardner, Jr. |
| 2008/0208020 A1 | 8/2008 | Cinbis et al. |
| 2010/0046826 A1 | 2/2010 | Dirix et al. |

FOREIGN PATENT DOCUMENTS

| | | |
|---|---|---|
| JP | 2007-252693 A | 10/2007 |
| JP | 2008-008794 A | 1/2008 |
| JP | 2008-132335 A | 6/2008 |
| JP | 2009-066119 A | 4/2009 |
| WO | 93/16629 | 9/1993 |
| WO | WO 93/16629 A1 | 9/1993 |
| WO | 2008/116835 | 10/2008 |

* cited by examiner

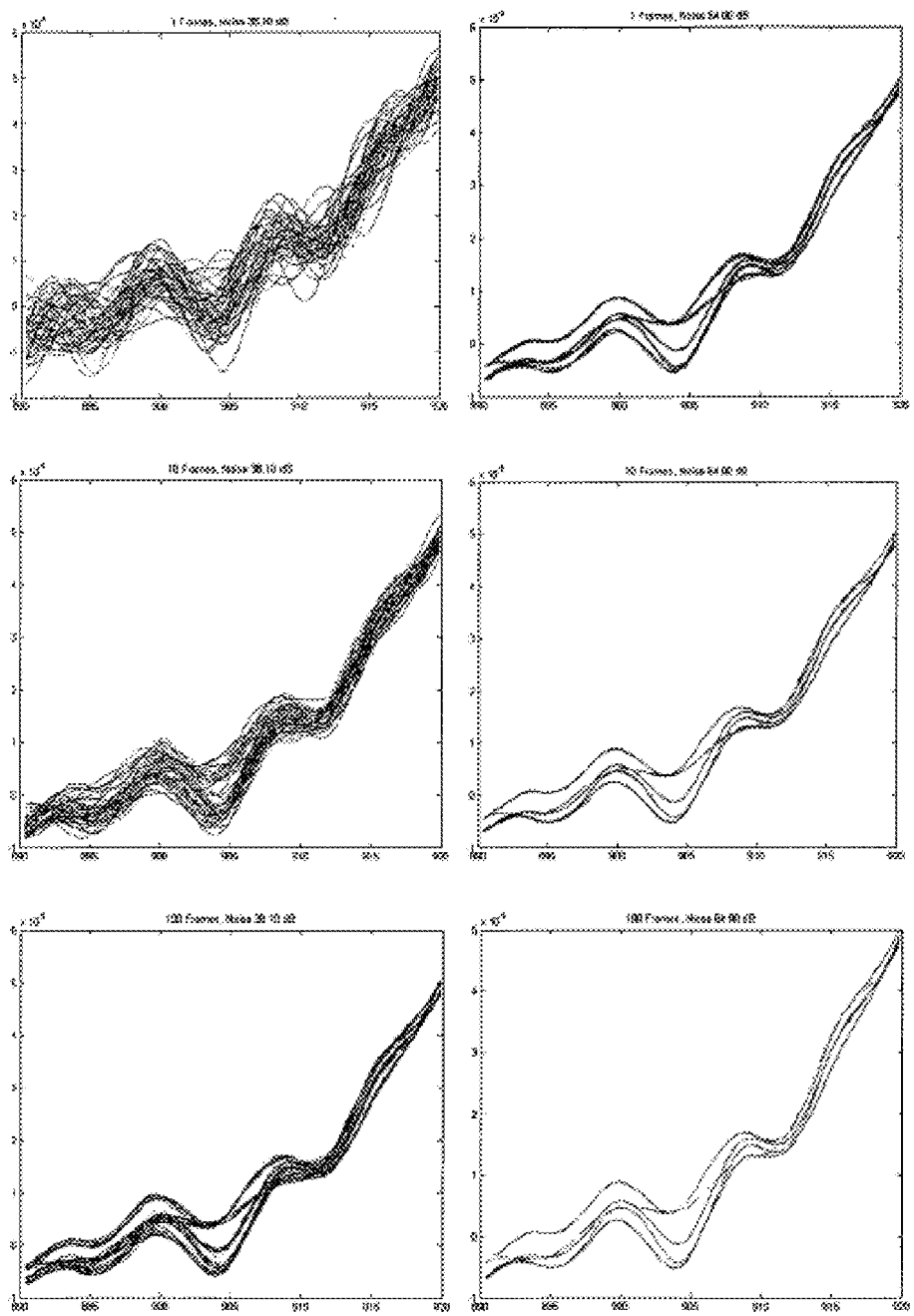
Fig. 8 (1)

DEVICE AND METHOD FOR DETECTING AND MONITORING INGREDIENTS OR PROPERTIES OF A MEASUREMENT MEDIUM, IN PARTICULAR OF PHYSIOLOGICAL BLOOD VALUES

The invention relates to a device and a method for identifying and monitoring contents or properties of a measurement medium, in particular physiological blood values, having the features of the preamble of the independent patent claims. Monitoring and measuring contents or properties of a measurement medium is currently undertaken in a multiplicity of medical and non-medical applications. By way of example, contents of the blood of a patient (e.g. blood sugar or oxygen saturation) or of process fluids (liquids or gases) of non-medical applications (e.g. process monitoring) should be identified online and monitored continuously.

By way of example, pulse oximetry is a method which determines the pulse rate (PR) and percentage oxygen saturation (% $SpO_2$) of the arterial blood. These days, this is an established method and is utilized in many fields of medicine, for example in intensive care, for monitoring sleep and during operations.

It is conventional in the underlying technology to record two wavelengths (typically 660 nm and 940 nm), which are generated by LEDs, with a great clock speed using an optical sensor. It is possible to extract the desired measurement values from different signal intensities in the variable and fixed regions. As a result of the tissue being transparent to the observed spectral range, additional signals can be generated in the case of strong and, in particular, varying external light as a result of changes. These are generally captured in each case by a third measurement point without LED illumination.

A general problem consists of the fact that the amount of light that can be introduced into the tissue in the case of optical measurement techniques is restricted. Otherwise damage to the tissue is to be expected as a result of thermal effects. As a result of this, the measurement times are comparatively long in known measurement methods or devices. This leads to a poor signal-to-noise ratio. However, the best possible signal-to-noise ratio is mandatory, particularly when measuring substances that are present in very small concentrations (e.g. when measuring blood sugar, where concentrations are measured in the region of mmol/l).

It is desirable these days to capture further blood parameters in addition to the oxygen saturation of the hemoglobin in order to obtain important parameters during patient monitoring.

First of all, it is important to monitor the gas balance in the blood. WO 2008/132205 A1 describes a sensor that can be used to determine the $CO_2$ partial pressure in the tissue in addition to the pulse oximetry.

Further important values for monitoring are the different hemoglobin derivatives. This includes determining the total hemoglobin concentration (ctHb), determining the carboxyhemoglobin concentration (HbCO) or other blood values. However, these additional blood values cannot be captured by the technology (2 wavelengths) described above. A precondition for capturing these is the very precise determination of the spectral properties of the arterial blood and of the tissue over a large spectral range.

Another blood value to be measured is the blood sugar content. Diabetes mellitus is one of the most common metabolic diseases worldwide and its prevalence is greatly increasing as a result of the changing dietary habits. Thus, the assumption is that in 2010 there was a prevalence of approximately 285 m persons (6.4% of the world population) and in 2030 this will already be 439 m persons (7.7% of the population). This is one of the reasons why the glucose concentration in bodily fluids is one of the most-determined parameters in clinical chemistry. Here, one would ideally like to determine the precise blood sugar level using non-invasive methods.

For patient monitoring, WO 2006/094169 A1 proposed an LED-based, photometric system for examining additional blood parameters, which system has a multiplicity of LEDs (typically 8) of different wavelengths and is therefore able to collect signals at different spectral nodes. However, this technology has a number of disadvantages. The LEDs are switched in sequence and recorded with a time offset by a broadband sensor and therefore often have virtual superposed signals in the case of varying external light influences and movements on the sensor. Since many LEDs, and hence nodes, have to be switched in sequence in this technology and since the evaluation must be predominantly carried out from the relative intensity of the signals with respect to one another, such superpositions have a particularly strong effect. Furthermore, LEDs have a temperature-dependent emission curve, and a spectral full-width at half maximum of between 20 nm and 30 nm usually underpins the LED emissions; this does not allow a precise restriction to a narrow spectral range and hence to a relevant chemical component. Furthermore, as a result of the small number of nodes in combination with the properties, which vary from person to person, of the skin surface and of the tissue, a precise separation and a quantitative evaluation of the blood components is only possible to a limited extent. It is only possible to generate ratios of a few nodes from the measurement and to use said ratios for analyzing the chemical components. However, since the spectroscopy of the blood and, in particular, the properties of the tissue through which light should pass (different scattering properties from person to person and also a wavelength dependency) have a great impact on the measurement results, measurements using this method are prone to errors.

These days, a variety of developments enable a reliable determination of the glucose concentration in the blood and in liquids such as blood plasma and serum derived therefrom, but also in other bodily fluids such as e.g. urine. Various enzyme-based methods in particular have been able to establish themselves in recent years. However, in this case, the majority of these methods demand that a small amount of blood be withdrawn and therefore these are part of the invasive methods.

The current practice of measuring the glucose ranges between seldom—when consulting a medical practitioner—and values measured a number of times per hour in the case of patients in intensive care units. In the case of insulin-dependent diabetics, self-monitoring taking place up to six times a day with the aid of test-strip instruments is conventional for obtaining an improved, but not ideal, regulation of the blood glucose concentration. Such measurements require blood withdrawal, which the patient finds uncomfortable. Moreover, as a result of being pressed out, the blood is not always in equilibrium with the tissue fluid. This leads to inaccuracies.

Hence the development of a non-invasive method and an associated device would be very desirable for medical engineering.

In order to determine the blood sugar, it is necessary to determine the glucose concentration quantitatively in the blood.

Spectroscopic methods which allow a reagent-free determination of the glucose in complicated bodily fluids have already been developed. By way of example, spectroscopic measurements in the near-infrared range (NIR spectroscopy)

have already been disclosed. Here, small concentrations of glucose (approximately 2 mmol/l to approximately 30 mmol/l; target range 5.0 to 7.0 mmol/l) have to be detected. Furthermore, there is a very high water content present in the blood (typically greater than 80%), which therefore causes much stronger absorptions in NIR spectroscopy. Furthermore, the blood contains other substances in varying and unknown concentrations, and cross sensitivity has to be excluded. If there is to be a non-invasive measurement, it is necessary to perform a measurement in the body within the surrounding tissue and the influences of the different media are to be taken into account or to be separated out.

Furthermore, it is necessary to select a measurement point on the body in the case of a non-invasive measurement method. Advantageous measurement points do not always have the blood present separately, but rather have the blood embedded in tissue. Moreover, the tissue is coated by a layer of skin which has properties which differ from person to person and can also vary greatly over time. Thus, for example, the water content of the skin fluctuates strongly and depends, inter alia, on the activity of sweat formation. Furthermore, the skin has different structures and can have a subcutaneous layer of fat at many places, which layer of fat is firstly characterized by a much lower water content and secondly also has a much lower perfusion and therefore is not necessarily in equilibrium with the blood sugar in particular. Furthermore, it is often necessary to take account of the fact that bone tissue is also situated in the optical measurement region. Here, it is not self-evident that the bone tissue is in equilibrium with the contents.

The wavelength-dependent examination of chemical components can take place in different ways. The measurement can be carried out at discrete nodes. In general, this is referred to as a photometric measuring technique or as multi-spectral photometry and either it is carried out with a plurality of light transmitters with different wavelengths or broadband "white light" is used and use is made of a plurality of spectrally limited receivers (filter technology). These light transmitters with different wavelengths can be realized by LEDs or by lasers and by broadband illuminations and narrow-band filters over the photoreceivers. If LEDs are used, there is an additional technical difficulty in that, firstly, they have a relatively large radiation distribution and, secondly, the radiation distribution changes as the emitters heat up. By way of example, an example of this technology was described in U.S. Pat. No. 5,086,229.

These measurement techniques typically have three to approximately ten wavelengths or wavelength ranges, which are recorded and evaluated.

Nor is this measuring technique expedient for the application for determining blood sugar. Firstly, a plurality of nodes have to be realized with this measuring technique in the effective wavelength range between 800 nm and 1200 nm. Here, these nodes have to satisfy three requirements:

They have to lie on and outside of absorption bands of glucose and of water.

They have to be independent of cross sensitivity to other substances that can occur in the blood or tissue.

They have to be designed such that it is possible to calculate the different scattered signals and light paths, and hence the different basic signals, therefrom.

Hence, in conclusion, for a non-invasive measurement of the blood sugar content the following conditions have to be met: it must be possible by spectroscopic means to identify small glucose concentrations compared to water concentrations. Deep penetration through the tissue (typically more than 3 mm) is necessary. It must be possible to rule out cross sensitivity to other substances. It must be possible to distinguish between values from blood and tissue (pulsatile check). The instruments must be cost-effective and small and hence portable. The light source must not be too strong so that there are no burns on the finger; the light source should preferably be based on LEDs.

To date, it has not been possible to develop a mass-produced instrument which enables a non-invasive regular, secure and reliable blood sugar determination for a diabetic. Many of the previously proposed methods and device are not suitable for solving these problems or satisfying the aforementioned conditions.

A non-invasive sensor for measuring blood sugar has been disclosed in e.g. U.S. Pat. No. 5,070,874 and U.S. Pat. No. 5,360,004.

Moreover, reflective measurement techniques are well known. They have limited to no applicability for blood sugar measurements. Firstly, the predominant part of the radiation comes directly from the surface; secondly the skin has a structure that differs from person to person and also from point on the body to point on the body. Furthermore, it is not possible to define the scattering properties reliably. Therefore a stable quantitative measurement at the required low substance concentrations is not expedient for the stated problem using reflection-spectroscopic methods.

Spectroscopy is used for determining the concentration of organic materials and, as a fundamental technology, is often used in medical research. Here it is conventional to withdraw small quantities of blood and to examine the latter in vitro by photometric or spectroscopic means. The complexity in terms of instruments and performing this is significant for this invasive technology. Furthermore, there is a time delay. In vitro determination only has very limited use for patient monitoring.

In spectroscopic metrology, the light is split over a broad spectral range using a spectrometer, with use these days mainly being made of a grating structure and the light being recorded and analyzed in spectral fashion on a sensor with many photoreceivers (pixels) arranged in a line. A further option lies in the Fourier transform method (FTIR spectroscopy), which is preferably used in the near infrared.

This method is not ideal either for blood sugar determination. Firstly, this method is better suited to longer wave radiation. Secondly, even though it is well suited to narrowband peaks as a result of the Fourier principle, this is a relatively imprecise and error-prone measurement method in the case of broadband absorptions, which are required in the range between 800 nm and 1200 nm for the quantitative analysis of water and glucose in the blood.

The inventors have recognized that, for blood sugar measurements, use should only be made of methods in the spectral range between 650 nm and approximately 1200 nm because otherwise the possible path length in the tissue is too short and the influences of the skin and outer layers are too great. This spectral range is known as a diagnostic window in medical engineering. The range also renders it possible to analyze the substances under the skin surface. Furthermore, it is known that the effective path length of the light deviates strongly from the direct path length as a result of the strong scattering properties of the tissue. A typical variable for the estimation is a factor of 4 to a factor of 8 for the effective path length with respect to the direct path length.

However, since the plurality of known methods for blood sugar measurement measure at wavelengths above 1300 nm due to stronger signals of the absorption bands occurring there, only few of the known methods for determining the blood sugar remain.

Further approaches for determining the blood sugar were proposed by Fischbacher et al. (Ch. Fischbacher, K.-U. Jagemann, K. Danzer, U. A. Müller, L. Papenkordt, J. Schüler; *Enhancing calibration models for non-invasive near-infrared spectroscopical blood glucose determination*; Fresenius J Anal Chem (1997) 359: 78-82 Springer-Verlag 1997) and Meuer et al. (*Non-invasive glucose determination in the human eye*; Wolfgang Schrader, Petra Meuer, Jürgen Popp, Wolfgang Kiefer, Johannes-Ulrich Menzebach and Bernhard Schrader; *Journal of Molecular Structure, Volumes* 735-736, 14 Feb. 2005, pages 299-306 and Dissertation Petra Meuer, University of Würzburg 2002).

Fischbacher et al. show that a close link can be established. However, it was identified that the signal-to-noise ratio of conventional spectroscopy instruments was insufficient. Furthermore, measurements were taken in reflection mode, which is not productive in the tissue, as described above.

Meuer et al. also show good results in the measurements on the eyeball. As a result of the clear, non-dispersive medium, the proposed method can also be used in reflection mode. However, it was also shown clearly in this case that commercially offered spectroscopy techniques do not satisfy the necessary signal-to-noise ratio for reliably determining the low concentrations.

Further fields of application, in which contents of a measurement medium have to be established in a time-resolved fashion, relate to the measurement of lactate in the blood, the dialysis or the blood in a heart-lung machine, where blood values are likewise established (but optionally in vitro), or else to non-medical applications where, for example, process fluids are to be monitored. By way of example, typical non-medical applications include color measurements of liquids in production processes. It is likewise conceivable to measure gases in combustion processes. By way of example, further application options emerge in food technology when adding ingredients which are supplied continuously.

It has already been disclosed to use laboratory spectrometers for examining blood and tissue components in vivo. In accordance with the prior art, modern laboratory spectrometers these days operate using line sensors. Laboratory spectrometers usually work with glass fiber connectors, and so complicated optical waveguide solutions for illuminating and capturing light would have to be routed from the measurement point (sensor on the tissue) up to an instrument unit with a spectrometer. However, the time-resolved measurement can only be realized with poor signal-to-noise ratios due to simultaneous, in fact significant, light losses (particularly when coupling in light).

Therefore the application of such laboratory spectrometers is likewise not expedient for monitoring or measuring blood values such as e.g. the oxygen saturation or the blood sugar determination.

Monochromator systems and FTIR spectrometers do not satisfy the time requirements for combined spectral analysis and pulse monitoring.

A glass fiber can only capture a small portion of the effective light. The units therefore generally require long integration times during the measurement. EP 522 674 A2 has disclosed an oximeter for determining the blood oxygen saturation in a fetus. To this end, use is made of a spectrometer into which measurement light from a measurement point is transmitted to a spectrometer by means of glass fibers.

US 2006/0167348 has disclosed the practice of generating in-vivo infrared spectra using a conventional FTIR spectrometer. To this end, it is also proposed to transmit the measurement light by means of a glass fiber.

WO 2009/043554 has disclosed a method and a measurement apparatus for collecting spectrometric measurement signals from living tissue. However, it does not show how the measurement light is coupled into the sensor arrangement.

As a result of the spectrometers necessarily splitting light and the limited light intensity to which the skin surface of the body can be exposed, these measurements have therefore to date not been able to be carried out in a time-resolved, i.e. pulse-resolved, fashion. However, this would be necessary to distinguish between the pulsatile component and tissue component of the measurement values.

Furthermore, the sensors, or at least the parts that are attached to the body, must not exceed specific dimensions so that in practice they are not bothersome to a patient in the case of long-term monitoring.

A system for the spectral photometric measurement which records measurement values in a time-resolved fashion is proposed in WO 03/071939 A1. Here, a broadband light source is measured sequentially using different spectral filters. This system is very large and complicated. Moreover, the time-resolved information is always only recorded at one wavelength and the wavelengths are recorded in succession. Hence this system, which should also be used in a different spectral range and for monitoring the blood sugar, is not suitable for the long-term monitoring of pulse and blood parameters.

U.S. Pat. No. 5,879,294 proposes a system in which spectroscopic measurements of chromophores in the tissue are carried out. Here, the second derivative of a spectrum is used for the evaluation, and the evaluation is carried out at nodes (typically two per substance). This is how, for example, it is possible to determine the oxygen saturation in the tissue. This method can carry out the static, i.e. not the pulse- or time-resolved, quantitative determination of the chromophores. A method following therefrom for monitoring the tissue oxygen concentration ($StO_2$ concentration) is illustrated in WO 2007/048989 A1.

Moreover, for patient monitoring (for example for establishing the oxygen saturation), it is necessary to make a distinction between components in the blood (hemoglobin) and components in the tissue (myoglobin). The spectral properties of hemoglobin- and myoglobin-modifications are very similar, but different in the case of a spectrally highly resolved examination. A method which enables a distinction to be made is described in U.S. Pat. No. 5,931,779.

By contrast, a differentiation between tissue and blood is not mandatory when measuring blood sugar. Hence a pulse-resolved measurement is not mandatory when measuring the blood sugar. Precise values are achieved (if well-perfused tissue without e.g. subcutaneous fat and bones is present) if there is an equilibrium between the blood sugar content in the blood and in the tissue. However, the pulsatile component renders it possible to check whether there is an equilibrium.

A further, difficult constraint in the field of in-vivo blood analysis lies in the strong decrease in the absorption or molar extinction of the relevant blood, tissue and skin components over the spectral range between 500 nm and 850 nm, which is medically important for monitoring patients. Thus, hemoglobin and melanin which is contained in the skin have very large absorption coefficients in the visible spectral range, while these are significantly lower in the very near infrared range (VNIR).

When measuring blood sugar, which preferably is typically determined in a wavelength range between 800 nm and 1200 nm, there is lower absorption in the tissue, and so this problem carries less weight when measuring the blood sugar.

However, a comparable problem may also occur in the case of in-vitro measurement of blood values, e.g. in the case of dialysis patients or in the case of non-medical measuring and monitoring of process parameters at poorly accessible machine parts, e.g. in pipes. A time-resolved measurement is also required in the case of such applications and laboratory spectrometers with large dimensions cannot readily be brought to the measurement point.

All known solutions are therefore afflicted by disadvantages. In particular, there is no spectroscopy system which collectively satisfies all requirements in respect of a pulse measurement, in respect of an in-vivo blood analysis with a distinction according to pulsatile component (arterial blood) and static components (venous blood and tissue, myoglobin) and a miniaturization of the sensor unit for continuous use on the patient, in respect of a non-invasive blood sugar measurement or in respect of the measurement of the contents of a measurement medium at measurement points with a restricted amount of space.

The restrictions summarized above appeared up until now to make it impossible to carry out examinations in vivo and in a time-resolved fashion and/or with a device that has small spatial requirements and is robust.

It is therefore an object of the present invention to avoid the disadvantages of what is known and, in particular, to develop a device and a method which do not have the restrictions listed above and which, in particular, make it possible to carry out the desired analyses in vivo and in a time-resolved fashion, i.e. with the physiological distinction between arterial blood parameters and tissue-dependent parameters. Moreover, it should be rendered possible to carry out time-resolved measurements of blood sugar in vivo and blood measurements in vitro, or else time-resolved measurement in non-medical fields of application, in a reliable fashion and even at poorly accessible measurement points.

According to the invention, this object and further objects are achieved by a device and a method with the features of the characterizing part of the independent patent claims.

The theoretic basis for the spectroscopic or photometric examinations is given by the Beer-Lambert law. It can be used to determine concentrations $c_i$ of absorbing molecules in solutions when light passes therethrough.

$$I_\lambda = I_{0,\lambda} e^{-\mu_{\alpha,\lambda} l_\lambda}, \quad (1)$$

where $I_\lambda$ is the light intensity after passing through the substance to be examined, $I_{0,\lambda}$ is the irradiated light intensity, $\mu_{\alpha,\lambda}$ is the wavelength-dependent ($\lambda$) overall absorption coefficient and l is the path length through the substance. As a result of the scattering properties of tissue, an effective path length can be expected in this case, which is generally also wavelength-dependent, but this can be discarded in this spectral range and application case.

Algebraic manipulation yields:

$$\ln\left(\frac{I_\lambda}{I_{0,\lambda}}\right) = -l \cdot \mu_{\alpha,\lambda}. \quad (2)$$

This general law must now be diversified further because a substance such as e.g. human blood consists of many chemical component substances (molecular compounds) and the absorption coefficients of these differ in a wavelength-dependent manner. In the case of n substances, the following is obtained:

$$\mu_{\alpha,\lambda} = \Sigma_{i=1}^{n} \epsilon_{i,\lambda} \cdot C_i. \quad (3)$$

Under the assumption that that the path lengths remain the same for all wavelengths, this can now be written as follows for m wavelengths:

$$\begin{bmatrix} \ln\left(\frac{I_{\lambda_1}}{I_{0,\lambda_1}}\right) \\ \vdots \\ \ln\left(\frac{I_{\lambda_n}}{I_{0,\lambda_n}}\right) \end{bmatrix} = -l \begin{bmatrix} \varepsilon_{1,\lambda_1} & \cdots & \varepsilon_{n,\lambda_1} \\ \vdots & \ddots & \vdots \\ \varepsilon_{1,\lambda_n} & \cdots & \varepsilon_{n,\lambda_n} \end{bmatrix} \begin{bmatrix} c_1 \\ \vdots \\ c_n \end{bmatrix}. \quad (4)$$

This relationship can now again be written in the following form:

$$I(\lambda) = -l A(\lambda) C \quad (5)$$

or $$C = -\frac{1}{l} A(\lambda)^{-1} I(\lambda). \quad (6)$$

From this, it is possible to determine the concentrations of the substances directly.

An additional basis lies in the quantum chemical interaction between light and molecules. Thus, discrete and molecule-specific rotational-vibrational transitions or electronic transitions are excited by the wavelength-dependent absorption of light quanta. Here, the excitations occur in the observed spectral range as a result of the rotational-vibrational excitation of harmonic and combined vibrations of the molecules or as a result of complex electronic transitions in the chromophores. These transitions are wavelength-specific and substance-specific. Thus, the different substances can be analyzed at different wavelengths. However, since the human body, for example, contains very many different substances and the information therefrom becomes superposed, it is necessary to use the spectroscopic method in order to take account of the quantum mechanical interactions and not the node-based, multispectral photometry or photometric analysis.

In the case of a very detailed observation of the harmonic spectroscopy of the two substances water and glucose in the spectral range between 800 nm and 1200 nm, it is necessary, for example, to consider further details. Here, water is a very special molecule. Firstly, this is a result of the strong polarity of the water with the additional angled arrangement of the atoms. Furthermore, in the liquid state, the hydrogen bond has an influence on the spectra. Thus, on the one hand, the spectroscopy of liquid water is very strongly dependent on temperature. However, this can be discarded in this case because the temperatures at the measurement point in the body are fixed within a narrow temperature range between 35° C. and 40° C. A further influence results from the dissolution of the molecules in water. Thus, as the concentrations change, so do the forces between the molecules and the resulting spectra. Although these changes are relatively small, they are detectable and have to be taken into account in the chemometric evaluation.

The device according to the invention serves for identifying and monitoring the contents of a measurement medium, in particular for identifying and monitoring physiological blood values. The device has at least one light source for generating broadband light. In this context, broadband means that light is definitely generated with wavelengths that are suitable for analyzing the corresponding contents in the blood or tissue or in another measurement medium. Use is typically made of a light source which at least generates light in the frequency range between 500 nm and 850 nm for the purpose of monitoring patients (e.g. measuring the oxygen saturation) and at least generates light in the frequency range between 800 nm and 1200 nm for determining the blood sugar. In particular, the light source is a white LED which also generates a sufficient amount of light in the NIR range for blood sugar measurements. The light source serves for applying broadband light to at least one measurement region. The measurement region is typically a point on the surface of a living being, more particularly of a human, for example on the finger tip or on the earlobe. However, the measurement region can also be a pipe through which a medium to be measured flows, e.g. a line for transporting blood during a dialysis or a line which supplies fluids to a process or discharges them therefrom.

The device furthermore has means for spreading or dispersing the analysis light returned by the measurement point according to the wavelengths thereof. On the one hand, the analysis light can be light reflected directly from the measurement region or, on the other hand, it can be analysis light re-emitted from another point after transmission through tissue. The device furthermore has a sensor array for recording the spread light. The sensor array is typically a two-dimensional CMOS arrangement. Depending on the application and suitable frequency ranges, use can also be made of other two-dimensional sensor arrays, e.g. InGaAs sensor arrays. The CMOS image sensors are highly resolving and typically contain a million pixels or more (the sensor used here has 1.6 MP or even 5 MP).

A first advantage of using sensor arrays and typically CMOS sensor arrays lies in the simple availability thereof. However, in particular, two-dimensional sensor arrays also enable a higher measurement speed and better signal-to-noise ratios. As a result of the wavelength-dependent spread of the measurement light, the measurement light is imaged onto a row of the sensor. However, the measurement light has a specific width, and so the spread measurement light (i.e. the spectrum) can simultaneously be captured by a plurality of rows of the sensor array that are parallel adjacent to one other. As a result of a plurality of rows of the sensor array being read out in parallel, it is possible to add the results of the individual rows, i.e. the individual spectra can be added. It is typically possible to generate a spectrum by integrating the signals of up to 1000 adjacent rows of the array. To this end, the device moreover has means for simultaneously capturing the signals of a plurality of adjacent rows of a two-dimensional array. Moreover, the device is designed such that the spectra of these adjacent rows are added.

Thus, according to the invention, two-dimensional sensors are not used to carry out a spatially resolved measurement. Rather, the adjacent rows are used to generate more spectra within a short period of time and therefore generate better signals. Here, a parallel measurement is understood to mean a virtually simultaneous measurement. Naturally, it is clear that the individual pixels and rows of the sensor are read out sequentially. However, the scanning frequency is so high that it is possible to refer to this as a virtually simultaneous measurement of the parallel rows.

This achieves the read out of partial images and hence higher speeds. This makes it possible to generate better signal-to-noise ratios in the spectrum.

There are different requirements in respect of signal-to-noise ratios depending on the type of application. In the case of monitoring applications (such as, for example, measuring the blood saturation), it is only the arterial blood in many cases that is of interest. The tissue component is of no interest. It is for this reason that there should be a pulse-resolved measurement in such monitoring applications. Moreover, for the pulse-resolved measurement, the signal-to-noise ratio should, where possible, be such that a sufficiently clear signal can be obtained from the difference in the measurement between the systole and the diastole. A pulse-resolved measurement is less important when measuring blood contents such as e.g. blood sugar, fat or alcohol. By way of example, in the case of blood sugar, an equilibrium between the component in the arterial blood and the tissue component is reached after a relatively short time. In this context, a pulse-resolved measurement is not mandatory but can, by all means, be advantageous for checking the measurement results.

These days, CMOS image sensors are predominantly used in cellular telephones, surveillance cameras and digital cameras. High quality, miniaturized megapixel objective lenses are available particularly from the two first-mentioned fields of application.

Such sensors are very small, having typical image-edge sides of 3 mm. Furthermore, the can be parameterized for the read out region. Thus, very high frame rates of e.g. more than 100 Hz can be enabled in the case of a reduced image area, which high frame rates also enable a time-resolved evaluation of the pulsatile signal.

In the case of CMOS sensors, the electronics are directly integrated into the sensor. The optical arrays have circuits such as e.g. read-out circuits, adjustable amplifiers and analog/digital converters. This makes it possible to transfer data quickly and by means of thin cables. The whole arrangement containing spectrometer, illumination, electronics and image recording can thus have a very small design (preferably less than 20 mm×30 mm×100 mm, typically approximately 10 mm×15 mm×50 mm). Such a device can therefore be provided only with a thin electrical cable and can be directly attached to the patient. It is possible to dispense with glass fibers, etc. As a result of the designs of the CMOS arrangements with dimensions of a few millimeters, these have enough space in a miniaturized system, for example on the finger or on the earlobe or at points at which the available space is restricted.

As a result of the image quality, which in the meantime has become very good, and the low light requirements, it is also possible to use small, miniaturized illumination units.

Since the CCD arrays partly used in the prior art always require the whole detector to be read out, it proves impossible to achieve sufficiently high frame rates because CCDs have rates of a few Hz. It is possible to restrict CMOS sensors to a "region of interest" (ROI) and thus make these faster because it is only necessary to read out the required data. Although CMOS sensors likewise have a relatively slow frame rate in the case of a full image, frame rates of typically up to 200 Hz can be achieved in the case of a restriction onto a ROI.

This also makes it possible to record the spectra so quickly that it is possible to work in pulse-resolved fashion. The maximum pulse is typically 3 Hz. In the case of fourfold scanning, there would thus be the need for approximately 12 Hz.

An in-vivo measurement of blood parameters can be carried out on the basis of the pulsatile component of the signal. As a result of distinguishing between pulsatile and static components, it is possible to distinguish between the influences of the blood and those of the tissue. This influence and a possible evaluation thereof are also described in DE 195 18 511.

There is a doubling of the basic frequency as a result of the dichrotic notch. Since the Fourier analysis of the frequency content of the blood-pressure curve can contain components up to the eighth harmonic, scanning at 50 Hz is expedient from a technical point of view.

Moreover, quick scanning reduces movement artifacts which generate high-frequency signal components. If the sampling theorem is violated, such interferences are mirrored directly in the useful range of the signal.

If approximately 1000 spectra are recorded at 50 Hz in adjacent rows of the sensor during each image recording, which spectra generate a sufficient data depth and signal-to-noise ratio as a result of addition or integration, it is possible to evaluate spectrally for the blood components not only the tissue component but also the pulsatile component (arterial blood with approximately 1% of the signal as spectrum).

The sensor array is arranged such that light with different wavelengths impinges on different points on the array. Moreover, the spread light preferably is, in parallel, guided onto a plurality of adjacent rows of the sensor.

The basic principle of the device according to the invention and the advantages thereof are the same for the various applications. The frequency range should be modified depending on the contents to be measured. Accordingly, light sources, sensors, diffraction gratings and the utilized optical units should be adapted to the measurement situation. The invention will be explained in an exemplary fashion in detail on the basis of determining blood values during patient monitoring and on the basis of a blood sugar measurement.

The device preferably has a housing and is designed as a compact assembly. The compact assembly contains at least the light source, the means for spreading the analysis light and the sensor array. Thanks to this arrangement, it is possible to integrate the illumination and spectroscopy system directly into the sensor at a measurement point. The illumination and the miniaturized spectrometer can be applied directly to the measurement region. As a result, it is possible to dispense with the relatively rigid and large optical fibers. Significantly more light is available.

If light is transmitted to the measurement point through a glass fiber, a large part of the power is already lost. If the glass fiber couples into the tissue and the returned light is picked up again by another glass fiber, a majority of the light is once again lost. Moreover, if only a slit is decoupled and spectrally spread for a spectrometer, only a small amount of light remains for the detection. This leads to the largest technically available lamps being used in known arrangements and, at the same time, to work being conducted with long exposure times.

In contrast to this, a very small light source (e.g. an LED) and a spectrometer in a housing are preferably brought directly to the tissue. This increases the light yield, and so the exposure times are very short.

The light source, the means for spreading the measurement light and the sensor array enable a spectroscopic analysis of the blood and of the tissue in the region of the measurement region.

There are different methods in the field of spectroscopy. Here, a new method is the field of spectral imaging. Here, light is spectrally split onto two-dimensional sensor arrays via efficient grating/optical unit arrangements. Spatial information is thus obtained in one direction on the sensor, while the other direction contains spectral information. Here, each individual image point is a pixel which obtains intensity information with usually a data depth of 8, 12, 14 or 16 bit. CMOS image sensors, which contain advantageous properties particularly for the invention described here, have prevailed in this technology. Here, InGaAs sensors are suitable for the longer wave spectral range, but these also have individual photoelements which have integrated the necessary circuit logic onto a CMOS pad.

According to the invention, use is preferably made of such diffraction gratings as means for spreading the measurement light and such sensor arrays for recording the spread light.

The wavelength-dispersive apparatus thus preferably comprises a dispersive optical element, generally an optical grating, more particularly a holographic grating, which, in an advantageous embodiment, is a blazed grating in order to enable a high light yield in the diffraction order captured by the camera or the image sensor and in the suitable wavelength range between e.g. 500 nm and 850 nm for measurements of $SpO_2$ concentrations or between 800 nm and 1200 nm for blood sugar measurements.

For blood sugar measurements, the spectral range is defined as approximately 800 nm to 1200 nm. In this spectral range, the strongest signal variations were detected in the region of 960 nm +/−50 nm and 1150 nm +/−50 nm. The spectra exhibit the correlation with changing water signals. The InGaAs sensor technology makes it possible to evaluate both regions at the same time. However, the currently commercially available sensors are significantly worse than the CMOS sensors in this spectral range; however, the latter only receive light up to 1100 nm. Thus, the InGaAs sensors have a significantly smaller number of pixels (typically 100 k pixels to 1000 k pixels), and hence a worse signal-to-noise ratio.

The maximum diffraction efficiency can be selected such that it falls into the wavelength range in which the utilized sensor has the lowest sensitivity. By way of example, the blaze grating can be a transmission grating with an asymmetric saw tooth-shaped grating profile, wherein the saw tooth flanks are respectively designed as individual mirrors such that they transmit the light in the direction of the desired diffraction order. Furthermore, it is also possible to use holographic gratings. Thus, for example, it is possible to use VPH gratings (volume phase holographic gratings) as specific blaze or holographic gratings. These VPH gratings are transmission gratings, in which a transparent, photosensitive material is enclosed between two glass or plastic panes, in which a desired pattern of a varying refractive index was produced, e.g. as a result of holographic exposure and a change in the structure of the material resulting therefrom. According to the invention, the use of such blaze gratings can achieve high efficiencies of more than 80% of the diffraction intensity in a small, predetermined wavelength range.

Thus, a very small spectroscopy system can be created by a diffraction grating and an entry slit, which spectroscopy system firstly covers the whole spectral range and secondly has a time resolution, which is important for the pulse-dependent recording. Moreover, as a result of the two-dimensional image acquisition it is possible to record and evaluate many spectra at the same time, which leads to a significant improvement in the signal-to-noise ratio.

This combination of technologies renders it possible to construct small, high resolution and very quick sensor units, which can be attached directly to the points on the body conventionally used for pulse oximetry.

This enables sensors that can be attached to preferred measurement points such as finger tips, balls of the hands or earlobes or to skin surfaces. The housing is therefore particularly preferably designed to be affixed to a point on the body of a human patient, in particular to fingers or earlobes.

The measurement quality in the body depends significantly on the selected measurement point. Particularly for measuring the blood sugar, the point must be well perfused, should contain little fatty tissue and be easily accessible for measurements. Therefore the following measurement points in the aforementioned sequence lend themselves to the measurement of blood sugar in particular: transmission through the finger, balls of the hands or earlobes. In the case of the finger, care has to be taken that the measurement is performed without bone or fingernail where possible. It is therefore an option to couple the light laterally into the finger and pick it up on a line centrally on the finger tip.

This proposed combination of technologies enables the following, very important sensor properties: the sensors have a pixel resolution that enables a whole spectrum to be recorded at the necessary spectral resolution of less than approximately 5 nm.

There is the option of reading out portions of the sensor and therefore of recording and reading out high read-out rates (typically greater than 100 Hz) and therefore of evaluating the spectral tissue and blood properties in a pulse-dependent fashion.

Moreover, the device particularly preferably has a slit aperture. The slit aperture is arranged between an inlet region for the analysis light and the means for spreading the analysis light. The slit aperture renders it possible to define a measurement region precisely. In particular, with respect to the means for spreading, the slit aperture is arranged such that an elongate image is spread open in a direction different from, preferably perpendicular to, the extent of the image. This makes it possible to obtain on a two-dimensional sensor array a representation resolved according to the wavelengths in one direction and a spatially resolved representation from the measurement region in the other direction. Moreover, the device is particularly preferably provided directly with an analog/digital converter. Current CMOS image sensors typically already comprise such analog/digital converters. However, according to the invention, the spatially resolved representation is not used for the spatially resolved analysis. Rather, the parallel measurement of a plurality of spectra by adjacent rows serves to improve the signal.

In the present case, an aperture is understood to mean any optical means which cuts out an elongate strip-shaped region of the region imaged via the first imaging optical unit (objective lens). Here, the strip-shaped region is not necessarily contiguous but can also, for example, be composed of a sequence of individual image elements.

The device moreover preferably has an amplifier for the signals, which can be parameterized from the outside. CMOS image sensors often already have such integrated amplifiers that can be parameterized from the outside.

As a result of the digital conversion of the signals in the circuit, the digital signals can be transmitted easily without loss and electrically over relatively large distances to an evaluation unit.

The light source is preferably an LED. LEDs are light sources that can be switched very quickly (typically 10-1000 μs). They operate without thermal problems with high light powers which are, however, not critical to the tissue.

For use in patient monitoring (e.g. oxygen saturation in the blood), use is preferably made of light in the visible (VIS) and near-infrared (NIR) spectral range, particularly in the very near infrared range, e.g. in the VNIR range between 500 nm and 850 nm. This light is preferably generated by an LED or a combination of LEDs. By way of example, conventional white-light LEDs are suitable for this, which white-light LEDs have a broadband light emission as a result of an additional superposed fluorescent dye. Inorganic fluorescent dyes, which for example have ytterbium or other rare earths in YAG or similar host lattices, can be used as dyes.

As a result of combining different dyes it is possible to generate light in the whole spectral range required depending on the application; thus, for example it is also in the range between 800 nm and 1200 nm for blood sugar measurements. However, it is also possible to combine light from different LEDs. However, in this case it has to be noted that the emitters must be temperature-stabilized and the radiation must be locally well homogenized.

The device furthermore preferably has a connector for electrical cables. In particular, the device moreover preferably has no connectors for additional optical lines for guiding light thereto or away therefrom. A thin cable with a few electrical strands is sufficient for the operation of the device according to the invention, particularly because high currents and high voltages are not required for the light source according to the invention and for sensors according to the invention and particularly if cables do not need to be screened for analog signals.

Thanks to the whole spectra being recorded it is possible to establish and monitor a multiplicity of different physiological blood values. In particular, it is possible to evaluate the following parameters:

Pulse frequency
Pulse shape and structure
Oxygen saturation Hb ($SHbO_2$)
Total Hb (ctHb)
HbCO concentration
Concentration of MetHb
Concentration of deoxygenized Hb
PI (perfusion index)
PVI (pleth variability index)
Tissue oxygen saturation $StO_2$
Concentration of the blood sugar
Lactose Within the scope of the present description, physiological blood values are all values which are established in a patient for diagnostic purposes or for monitoring, in particular the values listed above.

Moreover, various applications in the non-medical field are also possible, such as the monitoring of combustion processes (by measuring process gasses) or in the production of e.g. foodstuffs or pharmaceutical products when adding ingredients.

The device is particularly preferably designed for being applied in the case of both transmission and reflection measurements. As a result, blood components can be measured in the visible spectral range in a reflection mode and in the VNIR range in a transmission mode in order to compensate for the strong absorption between 500 nm and 850 nm.

If a sufficient amount of light can be irradiated thereon (or else depending on the measured wavelength), it is also feasible only to measure in a transmission mode. The problem of strong absorption in the range between 500 nm and 850 nm is no longer that pronounced in the case of, in particular, glucose measurements above 800 nm. However, if a sufficiently large amount of light is irradiated thereon, purely transmissive measurements are also feasible during monitoring, for example when measuring the oxygen saturation.

There are various options for implementing the combined recording in a reflection and transmission mode.

In a first embodiment for monitoring patients, the reflection recordings and transmission recordings are arranged sequentially in time. Here, light is alternately irradiated onto two regions of the skin. Light is first of all irradiated in the region of a line-shaped recording point and the reflection image is read out. In a next step, light is irradiated onto one or more points outside of the recording line and the light transmitted to the recording line is recorded and read out. The two items of information are linked to one another in the evaluation unit. In particular, the device is, to this end, provided with a computer arrangement, which is designed such that it is alternately possible to carry out a transmission measurement and a reflection measurement. Moreover, the device has a light source for this purpose, which light source enables light to be irradiated onto two different measurement points. This can be brought about by the use of a plurality of light sources or by the use of suitable deflection means.

In a second embodiment for monitoring patients, a spatial separation of the reflection and transmission regions is brought about. To this end, the device, and, in particular, the housing thereof, has means for separating the analysis light from a reflection region and a transmission region. The incident light is radiated onto a part of the skin which is situated in the field of view of the sensor. The second part of the field of view of the sensor is separated by a mechanical stop from the irradiated light. Hence only light that has passed through the human tissue can penetrate into this region.

The light which was reflected and emerged from the skin after the transmission can be imaged by means of an objective lens and an elongate aperture (slit) can initially extract a substantially elongate or one-dimensional image which can subsequently be spread, more particularly diffracted, in a wavelength-dispersive fashion in a direction that differs therefrom, which is preferably perpendicular thereto. As a result, it is possible to use relatively simple means to generate a two-dimensional image in a relatively simple manner, which image supplies wavelength-resolved information in respect of the skin and tissue region captured in a line-shaped fashion. As a result of the radiation being captured by an image sensor or image transducer, a subsequent analysis is made possible such that the substances contained in the skin and in the tissue can be established in a quantitative and pulse-dependent fashion and hence that it is possible, after a short time, to make statements in respect of the composition, in particular the chemical composition of the blood, by means of an in-vivo measurement.

Hence, according to the invention, it is possible to combine the functionality of a time-resolved and pulse-dependent sensor recording with a spectroscopic examination and analysis. As a result of the design, the light can be captured firstly in the reflection region and secondly in the transmission region.

The blood sugar content is determined in a comparable fashion, with a reflective measurement not being mandatory.

According to the invention, the slit can substantially correspond to the line direction of the recording point on the skin. The diffraction direction or the wavelength-dispersive direction can then run perpendicular to this slit direction, and so the rows and columns of a two-dimensional pixel array of the image sensor can correspond to these directions. Hence, an image emerges with a one-dimensional spatial component corresponding to e.g. the recording line on the skin and with a diffraction direction orthogonal thereto for establishing a diffraction image and the relevant spectra.

The lens system is advantageously designed with miniaturized objective lenses. To this end, use can be made either of megapixel objective lenses from the field of surveillance camera technology or of miniaturized objective lenses (e.g. polymer-based objective lenses), which already have a broad application in the cameras of cellular telephones. However, use can alternatively also be made of other lens systems or else of achromats for the imaging.

These objective lenses can be combined well with the utilized, very small sensors. Distortions which are often found in these very small objective lenses can due to their static nature be compensated for using software.

By way of example, the device according to the invention can have three imaging optical units or objective lenses. Of these, the first imaging optical unit generates a two-dimensional image of the illuminated region on the elongate or slit-shaped aperture, which is preferably arranged in the image plane of this first imaging optical unit. The second imaging optical unit then images the slit-shaped aperture to e.g. infinity, and so it serves to collimate the light strip that has passed through the gap. Arranged behind this second imaging optical unit is the wavelength-dispersive apparatus with the preferably optical grating, which enables the dispersive splitting of the light in the second direction.

The third objective lens in turn generates a back transformation of the aperture image which has now already been split in a wavelength-dispersive fashion. Hence a wavelength-spread image of the line recorded on the skin is obtained on the sensor.

According to the invention, the image sensor can therefore be positioned in the wavelength range optimized for the respective application and there it can, for example, cover only a relatively small solid angle range.

The first imaging optical unit can image the region to be analyzed on the slit of the aperture, and so the aperture effectively masks regions outside of the recording line. Hence, in principle, the use of the aperture also renders it possible by means of the arrangement to illuminate a slightly larger region than the region that is subsequently examined by spectroscopic means, which is restricted by the aperture.

The LED illumination source is preferably controlled in a pulsed fashion. As a result, it is possible to reduce the influence of extraneous light.

Moreover, there can be an internal black-value balance. New generation CMOS sensors have an internal black balance. The pixels on the edges are covered in black. These are also read out internally and are used internally for black-value normalization. Although this does not rectify the problem of extraneous light, it does rectify the usual problems of sensors drifting in the case of variations of temperature or variations in the feed electronics. As a result, it is possible to record images with very short exposure times and high light intensities. It is for this reason that extraneous light influences are generally small. If extraneous light influences can occur, it is possible, in each case, additionally to record a background image without LED illumination and with a greatly reduced ROI (region of interest; examined frequency range) and the image can be corrected therewith. A fixed white-light image of the illumination is stored in the evaluation unit prior to the sensor being used. In equation (1), this corresponds $I_0(\lambda)$.

After each recording, all approximately 500 to 1000 adjacent, spatially resolved spectra are added to a spectrum with a great data depth, and the value $I(\lambda)$ is created according to equation 5 above. Furthermore, the second derivative of a of the added spectrum is generated. This can be used to determine the necessary concentrations directly. When evaluating the time-dependent values, it is possible—as is conventional in pulse oximetry—now also to determine the values for the component of the arterial blood from the pulsatile component. If there now is the option of establishing the spectroscopic data in a pulse-resolved manner, it is also possible, for determining the blood sugar, to integrate the spectra of the systole and the diastole separately and to obtain the clean spectrum of arterial blood by simply forming the difference and therefore not to determine the blood sugar component in the tissue but rather to determine the blood sugar component in the arterial blood within the body.

The recorded spectrum varies as a function of the pressure with which the finger (or another measurement point) is pressed onto the sensor. This pressure dependence is avoided if the second derivative of the spectrum is analyzed. Moreover, the second derivative makes it possible to measure the absorption only with respect to the arterial blood. The effects of light scattering in the surrounding tissue are avoided. In certain circumstances, the effect of the contact pressure on the spectrum is greater than the absorption by the arterial blood. It is therefore important that it is possible to undertake measurements that remain unaffected by the contact pressure. This is possible when analyzing the second derivative.

It is also possible to sum different regions or to illuminate and analyze portions differently for the different evaluations.

It is advantageous for the pulse information to combine and evaluate relatively large regions of the wavelength-split information, particularly in the range between 520 nm and 570 nm. Since the pulse is present in the whole spectral range, it is alternatively possible to sum over all pixels for the evaluation. Thus, for example, in the case of a scanning frequency of 50 Hz, it is typically possible to integrate 500 000 pixels with 12 bit data depth per image, which results in a very large data depth and hence also makes it possible to detect very weak variations in the intensity as a result of the pulsation.

It is possible to record the perfusion index PI according to the formula $$PI = \frac{AC}{DC} \times 100\% \tag{7}$$

from the pulse information as the ratio of the pulse amplitude to the fixed, time-unchanging absorption by the tissue and the venous blood. Here AC is the amplitude of the pulse-dependent signal and DC is the maximum absorption signal. This PI value is dependent on the wavelength, but can be scaled according to the publication "The wavelength dependence of pulse oximetry" (Damianou, D.; Crowe, J. A.; Pulse Oximetry: A Critical Appraisal, IEEE Colloquium; volume 1996, issue 124, 29 May 1996, pages 7/1-7/3).

In the case of change, this variable provides an early indication of different, clinically relevant changes in the patient state.

A further important measurement variable is the "pleth variability index" (PVI), which establishes a correlation between respiration and pulse. The PVI is determined in multiples of the respiratory cycle by the formula $$PVI = \frac{PI_{max} - PI_{min}}{PI_{max}} * 100 * \%. \tag{8}$$

The calculation of the % SpO$_2$ concentration and the total hemoglobin values can be carried out as described in "The light-tissue interaction of pulse oximetry" (Mannheimer Ph.D.; Anesth. Analg. 2007 December; 105(6 Suppl): S10-7. Review) or in "LED Based Sensor System for Non-Invasive Measurement of the Hemoglobin Concentration in Human Blood" (U. Timm, E. Lewis, D. McGrath, J. Kraitl and H. Ewald; 13th International Conference on Biomedical Engineering; volume 23, Springer Berlin Heidelberg, 2009).

During the evaluation it is possible, comparable to conventional oximetry, to compare two spectral regions. By way of example, the spectral channels between 640 nm and 680 nm can be integrated to generate the usual signal at 660 nm. In doing so, it is typically possible, for example, to effectively integrate 50 000 pixels for generating the spectral measurement point.

However, the preferred evaluation is the chemometric evaluation of the pulsatile spectrum.

The concentrations of the different hemoglobin derivatives are determined directly from the quantitative, spectroscopic analysis.

Absorption maxima or -minima in the second derivative:

| | | |
|---|---|---|
| HbO$_2$ | 542 nm | 576 nm |
| Hb | 555 nm | 754 nm |
| HbCO | 538 nm | 569 nm |
| MetHb | 640 nm | |
| MbO$_2$ | 545 nm | 580 nm |
| Mb | 558 nm | 758 nm |
| MetMb | 628 nm | |
| H$_2$O | 730 nm | 830 nm |

It is possible, in an evaluation apparatus, to establish the spectral information which was generated very quickly in succession, wherein, for example, it is possible to carry out a multivariate statistical analysis, as is conventional in spectroscopy, in order to determine the spectral characteristic reflection or absorption components from the captured spectrum. Herein, it is possible to use different multivariate statistical analysis methods, such as e.g. correlation, regression, variant analysis, discriminant analysis and principal component analysis (PCA).

The computational evaluation can be performed in an evaluation apparatus which is separate from the device. If the measurement values are digitized in the device according to the invention and transmitted to a central evaluation unit via an electrical connection, it is possible that the transmission cables remain thin. At the same time, it is not required to design the sensor or the device according to the invention to be so large as a result of necessary computers, input devices or output devices that it is no longer possible to attach it to the measurement locations. An external evaluation apparatus also offers the possibility of temporary data storage or data evaluation by means of more complex mathematical methods.

As a result of the time-dependent evaluation, it is possible to distinguish between information from tissue and arterial blood. On the one hand, this blood information can be captured precisely from a theoretical standpoint by means of known molar extinction coefficients. On the other hand, it is also possible to evaluate a very weak water band at approximately 730 nm in the analyzed spectral range. Since the concentration of water in the blood always lies very precisely in the range between 80 and 85 percent by volume, it is possible to perform a second, independent calibration of the measurement in each measurement signal on the basis of the evaluation. The device, or more particularly the evaluation apparatus, can therefore also be designed to determine absolute values of the concentrations by means of the water signal.

A further advantage of the combined reflective and transmissive, spectrally resolved method is that the pulse signal can be captured more stably. In the visible spectral range, the average difference in the signal between pulse maximum and pulse minimum is, compared to the basic signal, significantly larger in the region of 570 nm than in the VNIR spectral range. This difference can be greater by a factor of up to 5. Furthermore, it is possible to integrate spectral ranges of interest during the pulse evaluation and so it is also possible to achieve a very high signal depth in the case of individual recordings, which can only be realized with great technical difficulties in the case of individual sensors.

In the application of the invention for measuring the blood sugar, it is possible to obtain very low glucose concentrations as a result of the improved signal-to-noise ratio by the 2D spectroscopy. Up to 1 million spectra are typically integrated. There are no problems with the skin because the selected spectral range achieves a sufficient penetration depth into the tissue. The measurement takes place in a time-resolved fashion. The high-resolution, spectrometric capture moreover serves for the evaluation and back-calculation by means of absorption signals and the second derivative of the absorption signals. The second derivative minimizes influences of the tissue scattering during the evaluation.

The whole typical spectral range from 800 nm to 1200 nm is recorded to evaluate the concentrations of the water and the glucose. The evaluation can be carried out using the raw spectrum or else using the second derivative.

Using the second derivative, it is possible to distinguish between measurement values resulting from measurement light being scattered in the tissue and measurement values from the blood.

It is possible to use chemometric methods such as PCA and PLS2 for a more precise quantitative evaluation. Here too it is possible to integrate a CMOS image sensor for the setting ROI, analog/digital conversion.

The image sensor can preferably already be monolithically integrated in a semiconductor component together with the evaluation apparatus and optionally with a control apparatus and optionally with a storage apparatus for reference data such that a compact and cost-effective design is possible and that complicated extra wiring can be dispensed with or maintained at low levels.

The light or the radiation emitted by the illumination apparatuses preferably has a spectrally homogeneous distribution over the wavelength range to be measured. Here, the illumination apparatus preferably emits collimated light. It is possible to use different broadband LEDs as illumination apparatus. It is also possible to use a light source with LEDs having other wavelengths and an additional superposed fluorescent dye, which generates a broadband emission in the spectral range between 500 nm and 850 nm for patient monitoring or in the range between 800 nm and 1200 nm for blood sugar measurements.

The illumination apparatus or the light source could be continuous but should advantageously be operated in a temporally pulsed fashion. Here, pulsed operation is advantageous in that firstly the recording apparatus is independent of changing extraneous light influences and secondly only very short moments of time are recorded.

According to the invention, the spectra can, during the analysis, more particularly be evaluated in the form of their white-normalized raw spectra and, additionally, in the form of their second derivatives, as a result of which the method can be carried out independently of instrument-dependent influences such as illumination variations or else broadband parasitic absorptions, which can be superposed as a result of different melanin concentrations in the skin or in tissue structures.

A further aspect of the invention relates to the use of the device described above for identifying and monitoring contents or properties of a measurement medium, e.g. for monitoring patients or, in a more general form, for identifying and monitoring physiological blood values of a living being, preferably during a non-invasive in-vivo measurement, but also during in-vitro measurements or in non-medical applications.

An even further aspect of the invention relates to a method for identifying and monitoring contents or properties of a measurement medium, in particular physiological blood values of a living being, and to a computer program product for carrying out this method. Here, a sensor with a housing is applied to a measurement region in a first step. In medical applications, the measurement region is typically a finger or an earlobe.

This can also be used to measure points in the body in the center of the body because, under certain circumstances (if the body restricts the function to the core region), the pulse identification in the extremities is only possible at these points.

Light from a broadband light source, which is arranged in the housing, is subsequently applied to the measurement region.

Analysis light returned by the measurement point is subsequently captured in a reflection mode and/or in a transmission mode. The captured analysis light is then spread in a wavelength-dependent manner and the individual, wavelength-dependent components of the captured light are imaged on a two-dimensional sensor array arranged in the housing. In particular, this is a two-dimensional CMOS array in this case. It is furthermore preferable for the light to be imaged on a plurality of parallel rows of the array. The spectra generated by the parallel rows are then added.

The spectrum generated thus is subsequently evaluated for the purpose of determining contents or properties of the measurement medium (typically for determining physiological blood values).

The returned analysis light is particularly preferably spread at a diffraction grating. This allows particularly compact devices to be provided.

It is particularly preferable for the returned analysis light to be captured both in a reflection mode and in a transmission mode. This can occur successively in time by alternating illumination of different measurement points or in parallel by capturing the returned light from different measurement regions.

It is particularly preferable for the captured light to be evaluated in a time-resolved fashion. As a result, a multiplicity of further values can be established and taken into account. It is particularly preferable for the second derivative of the captured spectrum or of the captured spectra to be determined for the evaluation. It is more preferable for the water content in the blood to be established at the same time during the evaluation and absolute values of the concentrations are determined on the basis of the established water component.

The invention will be explained in the following text using a couple of embodiments on the basis of the attached drawings. In detail:

Figure 6:
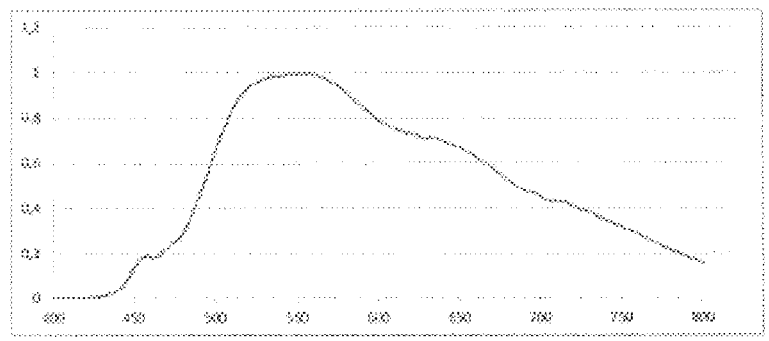
Figure 6:
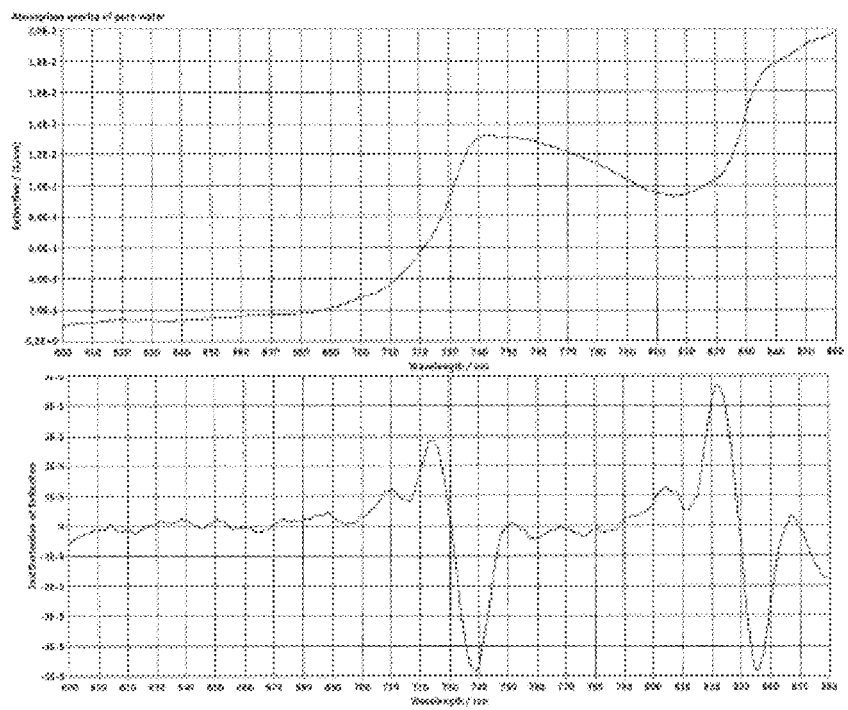
Figure 7:
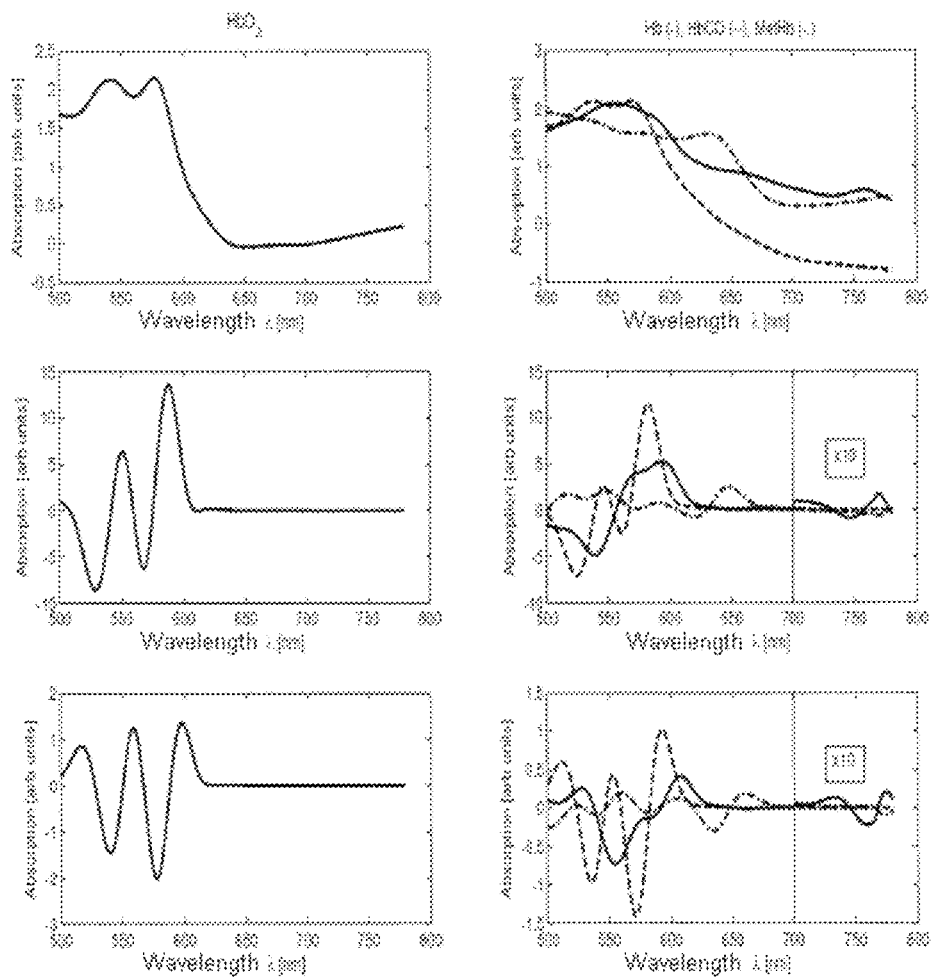

FIGS. 6a and 6b show the spectral distribution of a white-light LED illumination (FIG. 6a) and the absorption spectrum of water in the spectral range between 600 nm and 850 nm and the second derivative thereof (FIG. 6b); and FIG. 7 shows spectra of different blood constituents as absorption illustration and in terms of the first and second derivative thereof.

Figure 8:
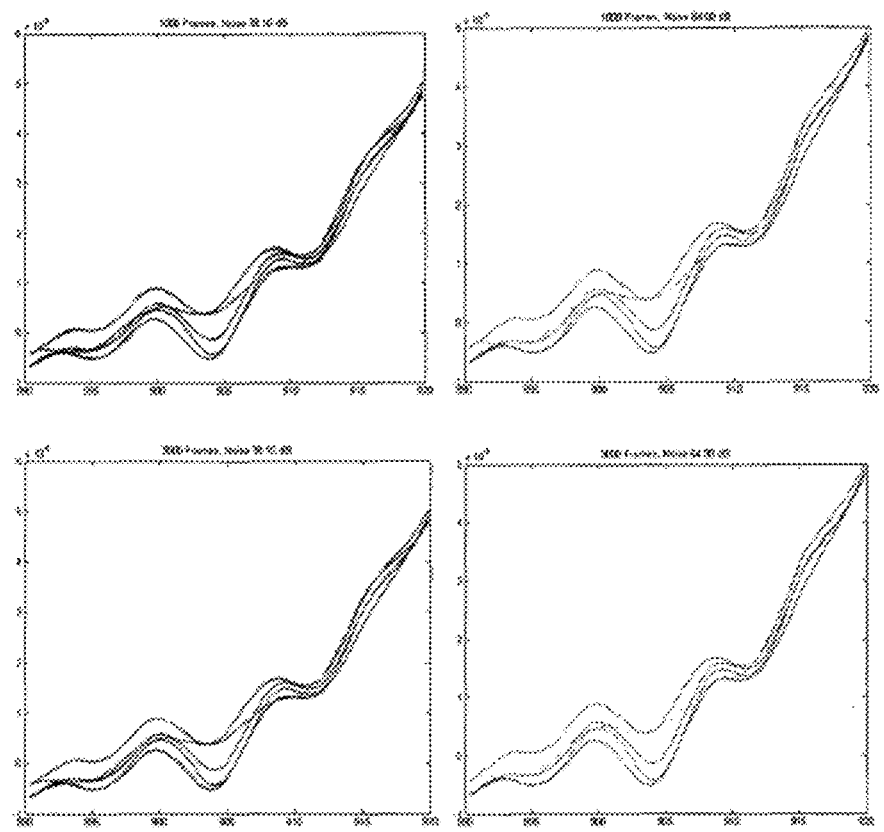

FIG. 8 shows an illustration of various spectra with various integrations and for two types of sensors (left 38 dB/right 64 dB)

Figure 9:
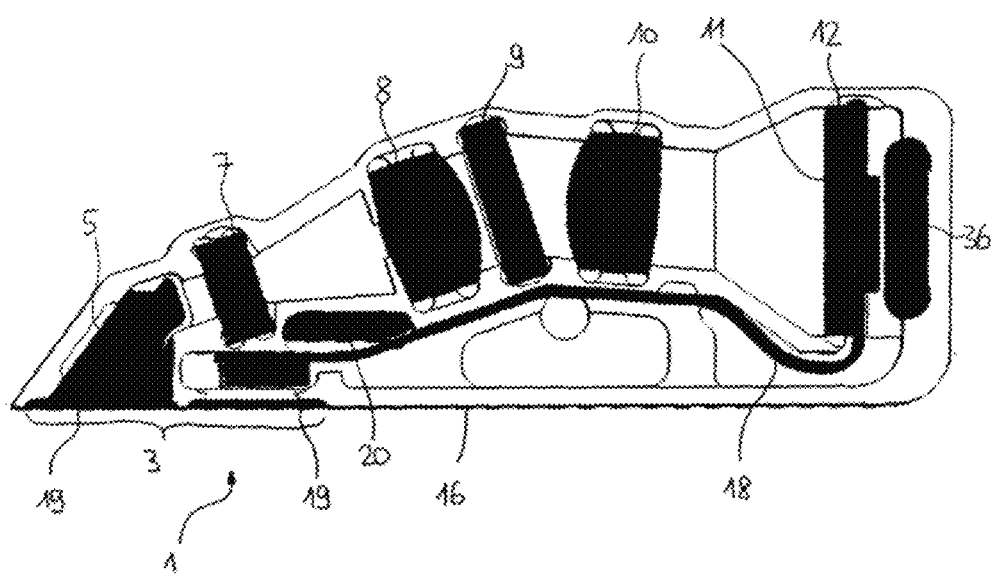

FIG. 9 shows a schematic illustration of a preferred sensor

Figure 10:
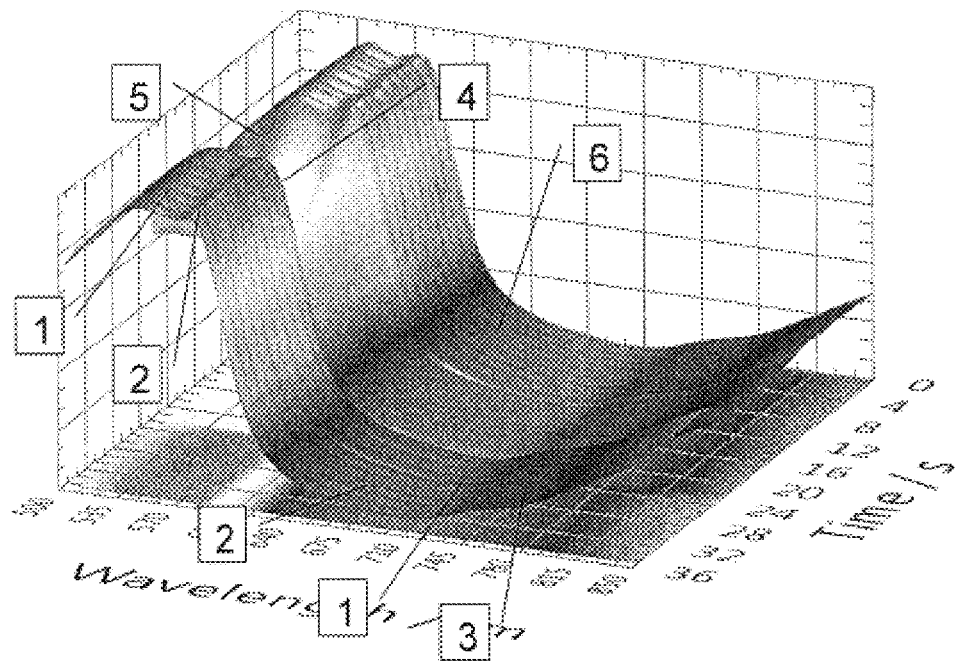

FIG. 10 shows an illustration of typical spectra

Figure 11:
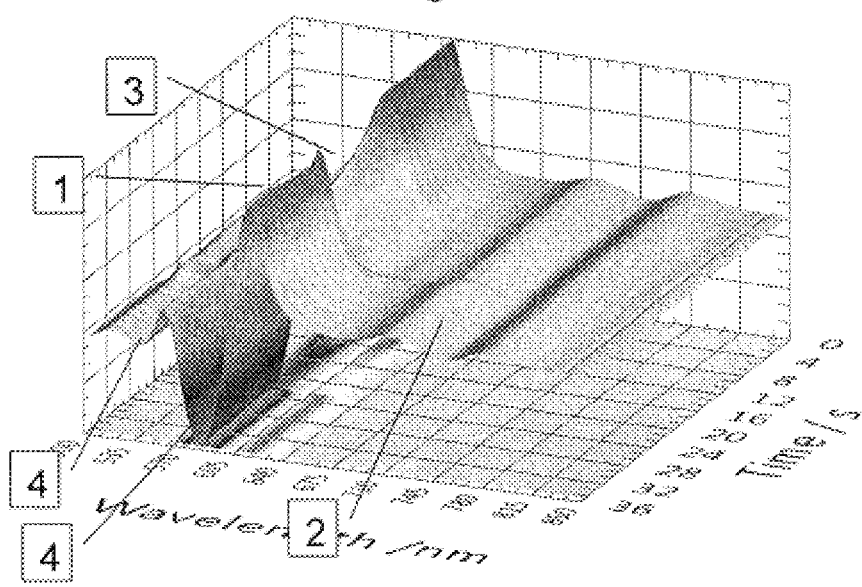

FIG. 11 shows an illustration of the second derivatives of typical spectra.

Figure 1:
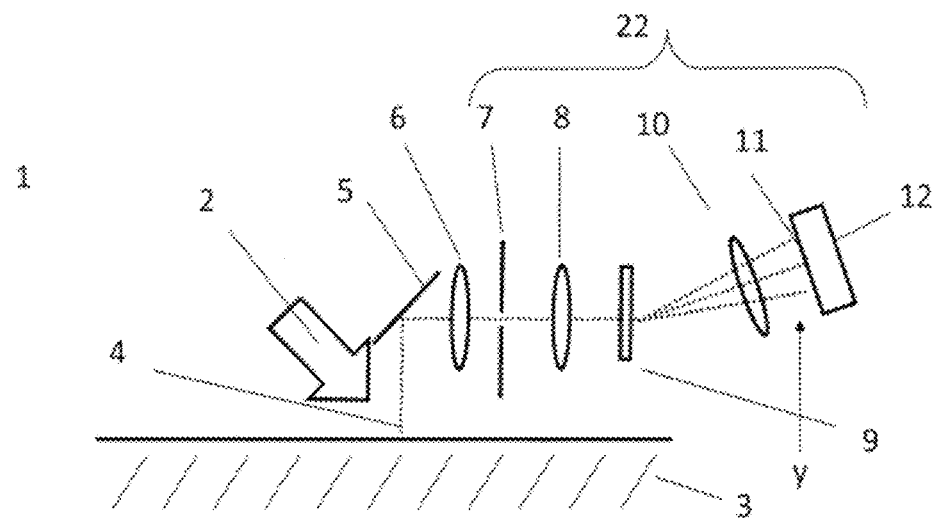
FIGS. 1a and 1b show a schematic illustration of a device according to the invention in a side view (FIG. 1a) and in a plan view (FIG. 1b)
Figure 1:
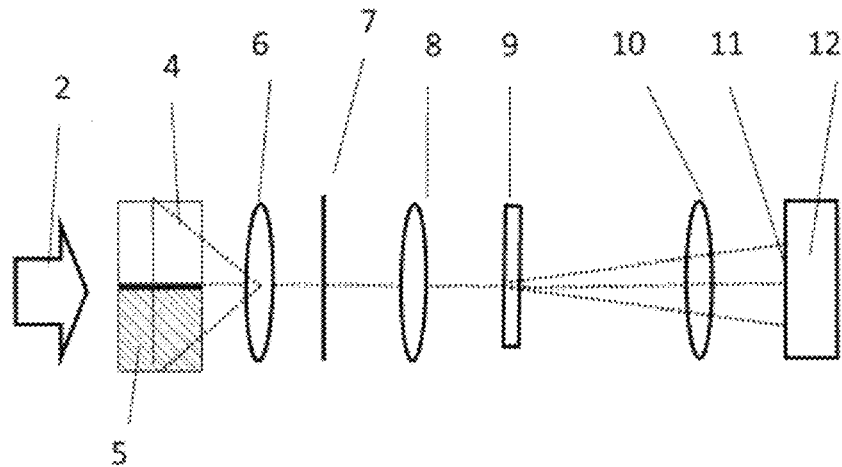

FIG. 1a illustrates a device 1 according to the invention in a side view. The device 1 has one or more illumination apparatuses 20 (see FIG. 4), which generate measurement light 2. Here, the illumination apparatuses 20 serve to illuminate a measurement region 3 to be examined, typically a skin and tissue region, as a substantially two-dimensional region or region with a relatively narrow extent in the Y-direction. In the various embodiments, the linear measurement region 3 is therefore respectively illuminated in a reflective or transmissive fashion by the illumination apparatuses and emits analysis light 4 in accordance with the transmission or reflection behavior thereof. The analysis light 4 is coupled into a spectrometer unit 22 via a deflection mirror 5. In order to determine the oxygen saturation in the blood and further blood values, the analysis light 4 in this case lies in the visible (VIS) and near infrared (NIR) range, e.g. in the wavelength range between 500 nm and 850 nm, and has a spectral distribution according to the substance composition, as will be explained further below with reference to FIG. 5. Hence the analysis light 4 contains spectra in the relevant wavelength range for identifying the quantitative substance composition in the measurement region 3, i.e. typically the substance composition of the arterial blood and of the tissue. The same device can also be used to determine the blood sugar concentration if the wavelength range is modified, typically to 800 nm to 1200 nm.

The analysis light 4 reaches an aperture 7 via a deflection mirror 5 and an imaging optical unit 6. The imaging optical unit 6 serves as entry objective lens for the spectrometer unit 22. The aperture 7 has an elongate design, preferably as a slit or slot, e.g. with a width of typically 10 µm to 30 µm, and extends in the horizontal direction or z-direction (perpendicular to the plane of the drawing in FIG. 1a). If further optical elements such as e.g. filters or further mirrors are inserted into the beam path, this should be taken into account accordingly; according to the invention, all that is relevant is that the measurement region 3 is imaged on the slit of the aperture 7 such that the extent thereof in the z-direction corresponds to the slit direction.

The strip of the image of the measurement region 3 which is allowed to pass through the aperture 7 is cast as light onto a diffraction grating 9 via a second imaging optical unit 8. For blood value measurements within the scope of monitoring, the grating is typically a transmissive "volume phase holographic" grating with a blaze wavelength in the region of 700 nm and approximately 300-600 l/mm. For blood sugar measurements, the grating is e.g. a "volume phase holographic transmission grating" with 600 l/mm in the region of 900 nm (producer: Wasatch Photonics). The grating 9 is designed and arranged such that there is a wavelength-dispersive spread of the analysis light 4 perpendicular to the direction of the slit in the aperture 7, i.e. in the transverse direction or y-direction; modified embodiments are accordingly also possible here. The diffracted light is imaged as diffraction image on a sensor surface 11 of an image sensor 12 via a third imaging optical unit 10. Hence, a diffraction image of the aperture 7 or the slit thereof is imaged on the sensor surface 11, with the longitudinal extent of the slit (the z-direction) in one direction and the wavelength-dispersive spread of the diffraction image in the other direction. For blood value measurements within the scope of monitoring, the image sensor is typically a CMOS camera sensor of the type Aptina MT9m032 (1.6 MP) or MT9P031 (5 MP).

By way of example, use is made of a sensor by Photonfocus (type A13121, 60 dB) or by Cypress (type IBIS5, 1.3 megapixels, 64 dB).

FIG. 1b illustrates a plan view of the arrangement.

Figure 2:
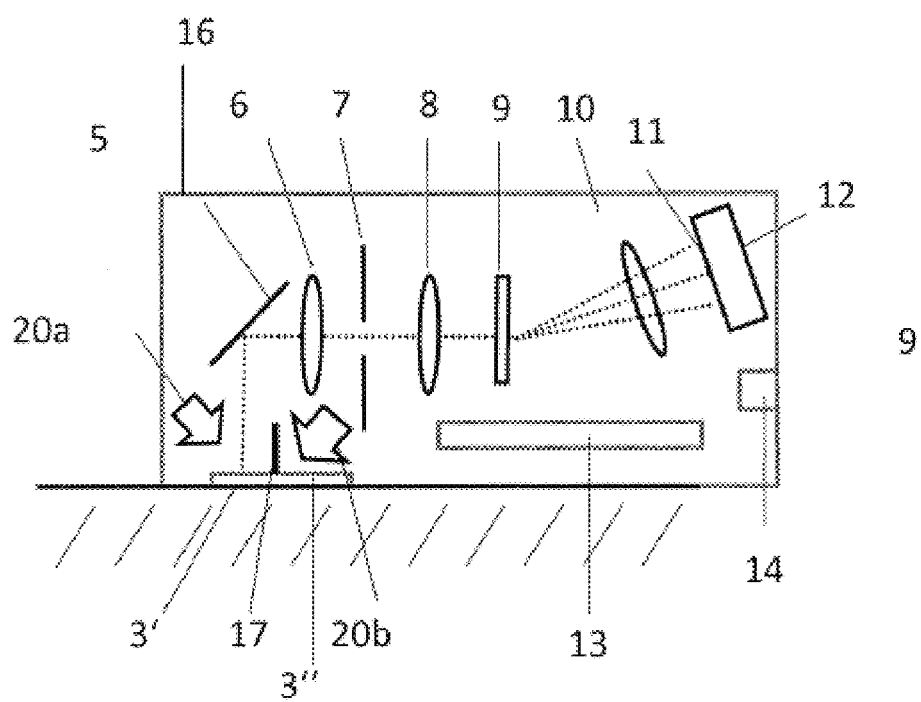
FIG. 2 shows a schematic illustration of a sensor unit.

FIG. 2 schematically shows a device according to the invention. The various components, in particular two light sources 20a/20b, the aforementioned mirrors 5, optical units 6, 8 and 10, the aperture 7 and the diffraction grating 9, are arranged within a housing 16.

Moreover, in the housing 16 there is also an electronics unit 13, which has a microcontroller (e.g. an FX2 component by Cypress) with fast serial data conversion (e.g. USB2/USB 3). The LED constant current regulators can also be housed here. A USB cable connector 14 enables the serial data transmission and the power supply of the sensor head.

The housing 16 is typically an injection-molded part made of a polymer material. If use is made of lenses from known miniaturized objective lenses with a housing diameter of approximately 12 mm, it is possible to achieve housing dimensions of the sensor of approximately 10×15×50 mm. Alternatively, use can also be made directly of objective lenses with housing diameters of 8 mm. The housing 16 has a shape as a result of which it can be attached to the measurement point, e.g. on the earlobe or on the finger or, in the case of applications in dialysis or in the non-medical field, also e.g. on lines for transporting the measurement medium. Moreover, the housing can additionally be provided with attachment means which are known per se to a person skilled in the art. In the region where the light exits or enters, the housing 16 is sealed with an anti-reflective glass window.

Figure 3:
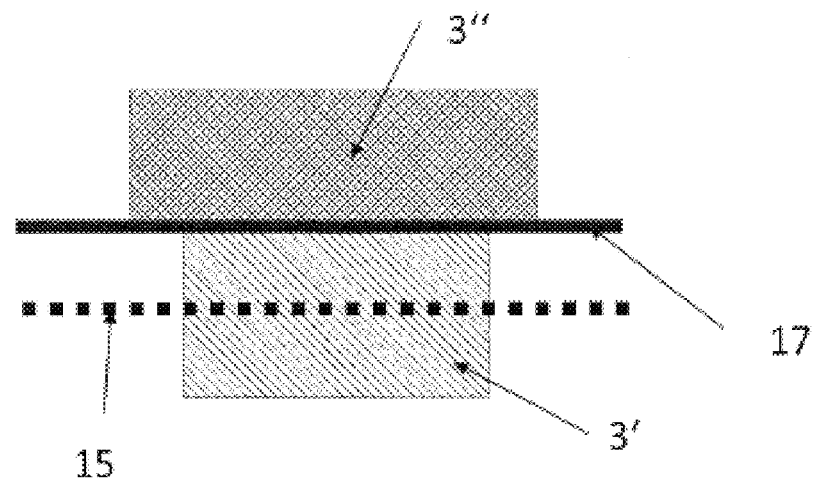
FIGS. 3a and 3b show an arrangement according to the invention for combined recording of reflective and transmissive properties in the case of time discrimination (FIG. 3a) and space discrimination (FIG. 3b)
Figure 3:
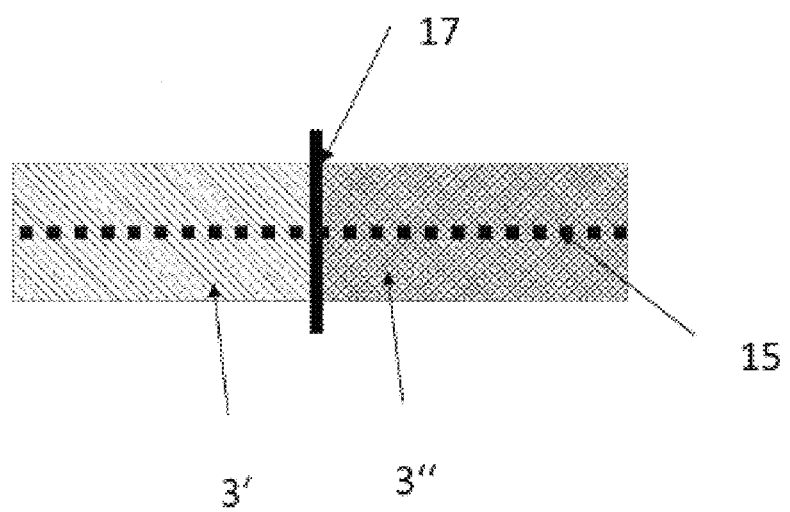

Here, a separating wall 17 separates two different irradiation regions 3', 3" for distinguishing between a reflection measurement (irradiation region 3') and a transmission measurement (irradiation region 3"), see also FIG. 3b in this context.

As a result of the strong change of the molar extinction coefficients in the spectral range, it is important to carry out the recordings both in a reflection mode and in a transflection mode. FIGS. 3a and 3b highlight two options for how this can be achieved using a sensor system.

FIG. 3a provides for a spatial-temporal separation. Here, first of all, there is a short, pulsed illumination of the region 3' (see FIG. 2) for a reflection measurement. In this case, the spectrometer unit 22 with entry objective lens is directed at the imaging line 15. After the image was read out, a second pulsed light source is activated, which illuminates the region 3" on the skin. Here the light cannot reach the recording line 15 directly through the separating wall 17. The light moves through the tissue in a transflective fashion, and, in the process, part reemerges at the recording line 15, which is then utilized for the transmissive evaluation of the signals.

In the option illustrated in FIG. 3b, the light is only irradiated into the region 3'. However, the 2D spectrometer unit is directed over the whole region 3' and 3" on the line 15. As a result of the spatial resolution on the array, it is possible to differentiate between light from the two regions 3' and 3". As a result of the separating wall 17, it is only a transmitted signal that is recorded in 3". The differences in intensity from the regions 3' and 3" that are to be expected on the sensor can be compensated for by a fixedly inserted neutral density filter in the beam path downstream of the inlet aperture 7 or upstream of the sensor surface 11.

Figure 4:
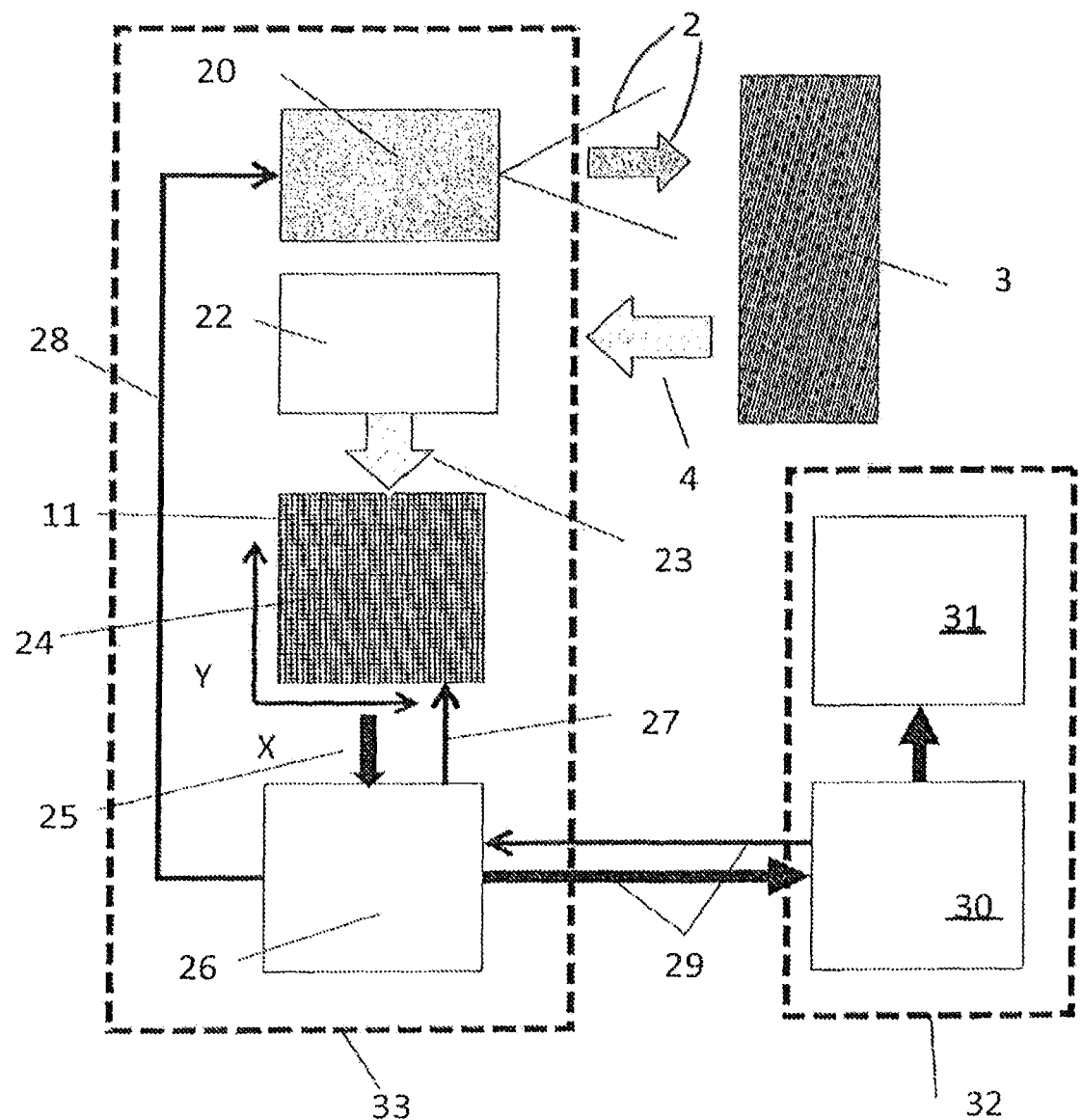
FIG. 4 shows a block diagram of the device according to the invention.

FIG. 4 shows a block diagram of an advantageous embodiment of the sensor system. The illumination unit 20 emits light 2 onto the measurement region 3. As described above, this light now is, in a reflection mode or transflection mode, coupled into the spectrometer unit 22 in a modified form as analysis light. After a spectral split in the spectrometer unit 22, spread light 23 is emitted to the image sensor 11. The image sensor 11 consists of individual photoelements 24 arranged in a matrix. The image sensor 11 is a two-dimensional CMOS digital camera sensor: as indicated in the block diagram of FIG. 4, it has a pixel array of individual pixels, which are sensitive in the VIS and VNIR spectral range and arranged in a matrix arrangement. In the one direction (e.g. the X-direction), components of the light at different wavelengths are imaged on the individual pixels as a result of the light being spread. A spectrum of the analysis light is therefore captured on one sensor row in the X-direction. A plurality of measurement rows of the sensor are parallel adjacent to one another in the Y-direction. A spectrum of the analysis light is measured on each of these rows. As a result of a plurality of parallel, adjacent rows, typically 1000 rows (or typically 2000 rows in the case of 4 MP or 5 MP sensors), being read out and added it is possible, according to the invention, to generate a signal with an improved signal-to-noise ratio.

The photoelectric signals are already amplified and digitized in the sensor. These signals are then transmitted in parallel or in series to a microprocessor 26 via a connection line 25. The microprocessor 26 firstly brings about a conversion of the signals; secondly, it also assumes the control of the LED illumination unit 20 via a control line and the parameterization of the image sensor 11 via a parameterization line 27.

Such a CMOS image sensor 11 renders it possible with a single image recording to record up to one thousand spectra, i.e. one spectrum per row, simultaneously, for example with a data depth of 12 bit. Each of these spectra therefore corresponds to the spectrum of one image element of the aperture, i.e. it corresponds to a subdivision of the slot-shaped aperture 7 as per the number of pixels of the sensor which are arranged next to one another in the Y-direction (see FIG. 1a).

The image sensor 11 can repeat the recording of an image with e.g. an image repetition rate of e.g. 50 recordings per second. Since, according to the invention, only a small spectral range in the range between 500 nm and 850 nm is relevant for e.g. monitoring applications or a small spectral range in the range between 800 nm and 1200 nm is relevant for blood sugar measurements, or else because only a restricted spatial region needs to be read out, it is possible to use partial image recording which is possible in such image sensors 11 such that partial images are set as "region of interest" (ROI), rendering it possible to read out only the set image region of interest (corresponding to a desired frequency range) of the image sensor 12 while at the same time maintaining the basic-data rate (pixel rate); this increases the number of transmitted frames, i.e. images or partial images, per second.

The microprocessor 26 moreover via a communication line 29 assumes the communication with a main processor 30 of the system. Here, the image data is transmitted to the main processor 30 and the main processor provides the sensor system 33 with the parameterization data. The power of the sensor system 33 is also supplied via the communication line 29. An advantageous embodiment of the connection is a USB connection, which simultaneously enables a high data transfer rate and a voltage supply with 5 volts. The main processor 30 is provided with a display and input unit 31, by means of which the system-relevant parameters can be set by a user and the currently established data can be illustrated. Processor, memory and user terminal can be housed in a unit 32, which can be set up at a distance from the patient. The main processor is typically a dual-core computer, with image processing taking place in the first core and the evaluation of the data for determining the tissue and blood values taking place in the second core.

Figure 5:
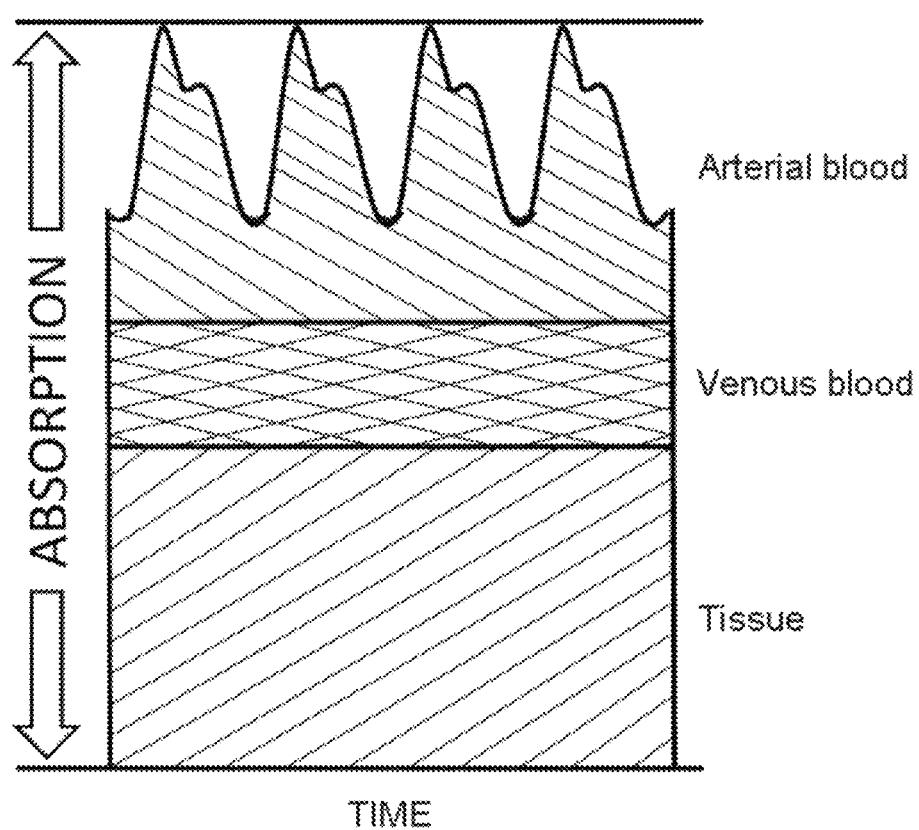
FIG. 5 shows the division of the absorption signals according to their origin.

FIG. 5 schematically illustrates the typical time profile of the signals during in-vivo blood measurement. Here, the optical signal has a constant component and a pulsatile component. The constant component, or, more precisely, the component which only undergoes long-term change, comes firstly from the venous blood and secondly from the tissue. Here, the signal from the tissue should furthermore be divided into two regions. One component is dependent on the contents of the tissue and the other component depends on the scattering properties of the tissue, which influence the real light paths. The pulsatile component is generated by the heart pumping the arterial blood. The absorption in the arterial blood is not the same at the systole and at the diastole. This allows a differentiation. Here, strongly oxygen-saturated blood is pumped into the measured body part. Here, the oxygen saturation of the hemoglobin in a healthy human lies in the region of 95% to 99%. The pulsating signal component is wavelength-dependent and depends on the measurement point and the measurement type (reflective/transmissive). Moreover, it makes a difference whether the measurement point is heated. In the case of finger measurements of healthy humans, the pulsatile component can (in the case of transmissive measurements) lie between 3% and 20%. In the case of reflective measurements, e.g. on the earlobe, the value can be 0.5% to 1.5%. The pulsating component is even lower in the case of patients with poor perfusion or acute problems.

The pulse and oxygen content or the blood sugar content must be determined from this small component. According to the invention, the spectra can be recorded very quickly (approximately 50-100 Hz) and approximately 1000 individual spectra can be added to form a spectrum in each recording. Using this, it is possible in spectroscopy to separate the constant and pulsating component in the spectrum.

FIG. 6a illustrates the spectrum of a typical LED illumination unit for monitoring applications. The system requires an illumination unit which provides light in the spectral range between 500 nm and 850 nm.

Shown here is the spectrum of a suitable broadband LED which, like a white-light LED, has a blue emitter (450 nm) for exciting a dye. This LED has a good intensity distribution, particularly in the spectral range between 500 nm and 650 nm. Depending on the field of application, use could also be made of a white-light LED with a substantially lower color temperature, use could be made of different dye compounds or additional monochrome LEDs could additionally be added to the illumination.

FIG. 6b shows the absorption curve of water and the second derivative thereof. Water has a weak absorption band at 730 nm and 830 nm (combination vibration $av_1+bv_3$; with a+b=4). However, this can be evaluated well using the technique presented here. Since the literature has disclosed that the water component in the blood of the human is very constant and lies between 80 and 85 percent by volume, it is possible, in the pulsatile component, to undertake an absolute determination of the concentration via the water signal as well. This can likewise be applied during monitoring and during e.g. the blood sugar measurement.

By contrast, blood sugar measurements require an illumination unit which provides light in the spectral range between 800 nm and 1200 nm (not shown).

FIG. 7 shows relevant spectra of oxygenated hemoglobin ($HbO_2$) and further hemoglobin derivatives as an absorption spectrum and as first and as second derivative, wherein the wavelength λ of 500 nm-800 nm is plotted on the abscissa. This very precise known data enables the calculation of the components of the substances using the previously described multivariate regressions.

What is important in this case is that the presented technique can be used not only to evaluate the absorption signals, but also to carry out a very precise delineation from the other substances by utilizing the second derivative. A multivariate statistical analysis method is optionally used for the evaluation. Individual spectra of all substances which are relevant and to be identified are advantageously measured and stored in advance.

FIGS. 8 to 11 show a specific design of a sensor and measurements made therewith.

FIG. 8 illustrates simulations of different spectra. The spectra in the left-hand column were generated on the basis of a first type of a sensor (with 38.10 dB). The spectra in the right-hand column were generated on the basis of a second type of a sensor (with 64 dB). By way of example, such a sensor is the 1.3 megapixel CMOS image sensor IBIS5-B-1300 by Cypress with 1280×1024 pixels with pixel dimensions of 6.7 μm×6.7 μm. For the purposes of the simulation, 5 very well measured spectra were taken as an initial point. From these, respectively 30 individual spectra are generated, onto which an artificial sensor noise is superposed. The result is plotted. It shows what scattering would be expected in the case of individual measurements.

From top to bottom, the various illustrations show the influence of the number of spectra integrations. The illustrations show the second derivative of the spectrum generated at a human finger, in the wavelength range between 890 and 920 nm. From top to bottom, the individual illustrations show the same number of (simulated) spectra, which were generated by adding a number of individual spectra, which number of spectra increases going down. Here, already 1000 rows are integrated in one "frame". The topmost illustration shows 1 frame. The bottommost illustration shows 3000 frames.

FIG. 9 shows a preferred embodiment of the device 1 according to the invention. In this figure, the same reference signs denote the same components as in the preceding figures. The device 1 has a housing, in which the various optical and electronic components are arranged. The measurement is performed on a finger. The finger is guided into the measurement region 3. This sensor is particularly suitable for measuring blood sugar. A broadband LED 20 typically emits light in the spectral range between 800 and 1200 nm in the direction of the measurement region 3. The housing 16 has an opening for the emergence of the light. The opening can be covered by a cover 19 that is transparent to the emerging light. The light re-emerging through the finger is routed into the housing 16 through a second opening in the housing 16, which is likewise provided with a cover 19 that is transparent to the light. The light is deflected onto a diffraction grating 9 via a mirror arrangement 5, a slit aperture 7 and a first imaging optical unit 8. The diffraction grating 9 spreads the light in a wavelength-dependent fashion and routes it to the sensor surface 11 of the image sensor 12 via a second imaging optical unit 10. The image sensor 12 and the LED 20 are arranged on a common printed circuit board 18 in the housing 16. The printed circuit board 18 is moreover provided with electronic components for controlling the LED 20 and the image sensor 12. In particular, the printed circuit board 18 also has a USB controller 36 and USB connectors (not illustrated in any more detail). This USB interface firstly enables an energy supply to the device 1. Secondly, it enables data interchange with an external computer or display instrument. Typically, 4×4 pixels are combined on the sensor (binning). The data combined thus is transmitted to a computer via the USB interface. There, the spectra are added after removing the static optical distortion of the sensor.

A high-power LED is used as an LED. Suitable achromats are used as lenses. The grating is a grating optimized according to the spectral range, typically having 300 l/mm or 600 l/mm.

FIG. 10 shows the time profile of a spectrum captured by the sensor as per FIG. 9. The spectrum was measured on a finger in the spectral range between 500 and 850 nm in a transflection mode (coupled into the tissue at one point and decoupled at another point on the same side). FIG. 10 shows the time profiles of the spectra with two different contact pressures (low contact pressure between 0 and approximately 10 s and from 20 s onward/higher contact pressure between approximately 10 and 20 s). The pulse can easily be identified in the spectral range between 520 and 580 nm as a result of the strong absorption of the oxidized Hb. The pulse can likewise clearly be identified in the range between 650 and 850 nm because the light penetrates deeper into the finger and more arterial blood contributes to the signal there. These two regions are denoted by the number 1 in FIG. 10. By contrast, in the case of stronger contact pressure between 10 and 20 s, the pulse is significantly less pronounced. Thus, care has to be taken, particularly in monitoring where a pulse-resolved measurement is important, that the contact pressure is not too great.

At the number 2 it is possible to identify characteristic band shapes of the oxygenated hemoglobin ($HbO_2$-arterial blood). There is a double peak at 540/578 nm. There is very low absorption in the range between 660 and 680 nm.

Number 3 in FIG. 10 shows an absorption band of the deoxygenated hemoglobin at 760 nm.

At shorter wavelengths, the absorption drops strongly at relatively high contact pressure (number 4 in FIG. 10). The absorption reduces because comparatively less blood is available (the blood is pressed out of the finger).

Displacements of the absorption double band (indicated by the number 5) provide information in respect of the content of HbCO in the blood.

The region at 650 nm denoted by 6 serves for identifying the methemoglobin content (MetHb).

FIG. 11 shows the second derivative of the spectra shown in FIG. 10. It is known per se to work with the second derivative of the spectra (derivative spectroscopy). It is possible to remove all constant components from the spectrum using this. As a result, it is possible to remove artifacts resulting from variations in the illumination, and also from different light levels as a result of the tissue scattering. Moreover, the significant information is amplified. The use of derivatives is particularly useful if the absorption maxima of components in mixtures of a plurality of substances only have minor differences or are superposed. The second derivative provides much additional information. The pulse can also still be identified in the second derivative. However, it is only pronounced where there is a large difference in absorption between arterial blood ($HbO_2$) and tissue/venous blood. This is particularly the case in the spectral range between 600 and 630 nm (denoted by number 1). The absorptions are less different in the longer-wave spectral range. The pulse amplitude of the second derivative is therefore significantly lower (see number 2 in the central region in FIG. 11).

The pulse is also less identifiable in the second derivative in the case of a strong contact pressure. At the number 3, there is not only a change in the pulse amplitude, but also in the shape and the position of the absorption bands when the pressure is increased. This shows that arterial blood in particular is pressed out of the finger when the pressure is increased.

The double peak of the oxygenated hemoglobin (indicated by number 4) is clearly identifiable in the second derivative.

The component of deoxygenated Hb (HHb) is greater in the tissue and in the venous blood. The absorption band significant in this case lies at 760 nm. It hardly changes as a function of the contact pressure since arterial blood is almost completely oxygenated. From the ratio between the intensity of this band and the oxygenated hemoglobin (identifiable by the double peak in the region 4), it is possible to determine the tissue oxygen saturation ($StiO_2$).

It is possible to determine the concentration of HbCO from the second derivative and, in particular, from the curve profile thereof and the positions of the individual absorption peaks. The concentrations can be determined as a result of the known, wavelength-dependent absorption coefficients of $HbO_2$, HHb, HbCO and HbMet.

In order to analyze the blood contents or the changes thereof, it is expedient to capture the data in a time-resolved (and hence pulse-resolved) fashion. This renders it possible, in a targeted fashion, to capture data separately from the systole and from the diastole, and also to analyze this separately (see also the illustration in FIG. 4, where high absorptions indicate the systole and comparatively low absorptions in the arterial blood indicate the diastole). In particular, the pure spectrum of the arterial blood component emerges from the difference between the spectra of the diastole and the systole. However, as shown in FIG. 5, the difference in the absorption between systole and diastole is comparatively small compared to the overall absorption. As a result of the large absorption overall, it is only low light signals that are still present on the sensor. Since, according to the invention, the spectra of a plurality of adjacent rows of a two-dimensional sensor are recorded simultaneously and added together, a signal with a sufficiently high quality is obtained. Therefore, it is also possible to evaluate very small difference spectra between systole and diastole.

The invention claimed is:

1. A device for identifying and monitoring contents or properties of a measurement medium comprising
    at least one broadband light source for generating broadband analysis light, [directly acting on a measurement region,]
    a dispersive optical element for spreading the analysis light according to the wavelength thereof, which analysis light has been returned by at least one measurement point or has passed through the measurement point,
    a two-dimensional sensor array for recording the spread analysis light, which two-dimensional sensor array is arranged such that light with different wavelengths impinges on different points of the sensor array, and such that the spread analysis light impinges on a plurality of adjacent rows of the two-dimensional sensor array such that the spectrum can simultaneously be captured by a plurality of rows of the two-dimensional sensor array,
    the device having a housing and being designed as a compact assembly which contains at least the light source, the dispersive optical element and the sensor array, the housing configured to position the light source for directly acting on the measurement region when the housing is aligned with respect to the measurement region and
    a computer arrangement which adds the spectra generated by the adjacent rows to improve the signal to noise ratio.

2. The device as claimed in claim 1, wherein the housing is designed to be affixed to a point on the body of a human patient or to a line for the measurement medium.

3. The device as claimed in claim 2, wherein the housing is designed to be affixed to the finger or an earlobe.

4. The device as claimed in claim 1, wherein the dispersive optical element is a diffraction grating.

5. The device as claimed in claim 4, said diffraction grating being a holographic grating.

6. The device as claimed in claim 1, wherein the device has a slit aperture, which is arranged between an inlet region for the analysis light and the dispersive optical element.

7. The device as claimed in claim 6, wherein the slit aperture is arranged with respect to the dispersive optical element such that an elongate image is spread open in a direction different from the main axis of the elongate image.

8. The device as claimed in claim 1, wherein the device has an analog/digital converter.

9. The device as claimed in claim 1, wherein the device has an amplifier.

10. The device as claimed in claim 9, wherein the amplifier can be parameterized.

11. The device as claimed in claim 1, wherein the device has a connector for an electrical communication connection.

12. The device as claimed in claim 1, wherein the device is designed to measure transmission and reflection.

13. The device as claimed in claim 12, wherein said computer arrangement is designed such that it is alternately possible to carry out a transmission measurement and a reflection measurement, with the device having a first broadband light source for carrying out a reflection measurement by illuminating a first measurement region and a second broadband light source for illuminating a second measurement region for carrying out a transmission measurement.

14. The device as claimed in claim 12, wherein the device is provided with means for separating the analysis light out of a reflection region and a transmission region.

15. The device as claimed in claim 1, wherein the device is designed for scanning with a frequency>50 Hz, with it being possible to establish a tissue component and a pulsatile component of the measured physiological blood values.

16. The device as claimed in claim 1, wherein said computer arrangement being designed such that the measurements can be carried out in a time-resolved fashion.

17. The device as claimed in claim 16, said computer arrangement being an external computer arrangement.

18. The device as claimed in claim 1, said computer arrangement being designed such that it is possible to establish a second derivative of the captured spectra and that physiological blood values in particular can he established on the basis of this second derivative.

19. The device as claimed in claim 18, said computer arrangement being an external computer arrangement.

20. A device as claimed in claim 1, wherein said computer arrangement is arranged external and wherein the device and the computer arrangement are or can be interconnected by means of a communication cable.

21. The device as claimed in claim 1, for identifying and monitoring wherein said contents or properties are physiological blood values.

22. The device as claimed in claim 1, wherein said broadband light comprises at least one of 500 nm to 850 nm and 800 nm to 1200 nm.

23. The device as claimed in claim 1, wherein said light source is a LED.

24. The device as claimed in claim 1, wherein said two-dimensional sensor is a two-dimensional CMOS array.

25. A method for identifying and monitoring contents or properties of a measurement medium, comprising steps of:
  applying broadband light from a broadband light source directly onto at least the measurement region,
  capturing analysis light returned in reflection and/or transmission mode,
  carrying out wave-dependent spreading of the captured analysis light and imaging the individual, wavelength-dependent components of the captured analysis light on a two-dimensional sensor array, for generating a spectrum,
  wherein the spread analysis light is imaged on a plurality of adjacent rows of the two-dimensional sensor array to capture the spectrum simultaneously by a plurality of rows of the two-dimensional sensor array,
  evaluating the spectrum generated thus for establishing the contents or properties of the measurement medium,
  wherein the spectrum generated by the individual rows are added for improvement of signal to noise ratio,
  wherein a housing is applied, in advance, to a measurement region, which housing contains the light source and the sensor array and positions the light source for directly illuminating the measurement region.

26. The method as claimed in claim 25, wherein the analysis is light is spread at a diffraction grating.

27. The method as claimed in claim 25, wherein the analysis light is captured in a reflection mode and in a transmission mode.

28. The method as claimed in claim 25, wherein the analysis light is evaluated in a time-resolved fashion.

29. The method as claimed in claim 25, wherein the second derivative of the captured spectra is established for establishing the physiological blood values.

30. The method as claimed in claim 25, wherein scanning is undertaken at a frequency of greater than 50 Hz and wherein a tissue component and a pulsatile component of the measured physiological blood values are established.

31. The method according to claim 25 wherein said content or properties are physiological blood values of a living being.

32. The method according to claim 25 wherein said two-dimensional sensor array is a two-dimensional CCD-camera.

33. The method according to claim 25 wherein said housing is applied in advance to a measurement region of a living being.

* * * * *